US011918602B2

(12) United States Patent
Sun

(10) Patent No.: US 11,918,602 B2
(45) Date of Patent: Mar. 5, 2024

(54) METHODS FOR REDUCING CHOLESTEROL WITH SUPERABSORBENT MATERIALS

(71) Applicant: SIMEON INVESTMENT, INC., Arcadia, CA (US)

(72) Inventor: Lijun Sun, La Canada Flintridge, CA (US)

( * ) Notice: Subject to any disclaimer, the term of this patent is extended or adjusted under 35 U.S.C. 154(b) by 67 days.

(21) Appl. No.: 17/327,037

(22) Filed: May 21, 2021

(65) Prior Publication Data

US 2021/0275572 A1   Sep. 9, 2021

Related U.S. Application Data

(63) Continuation-in-part of application No. 16/807,004, filed on Mar. 2, 2020, now Pat. No. 11,045,786, which is a continuation of application No. PCT/US2019/046077, filed on Aug. 10, 2019.

(60) Provisional application No. 62/717,644, filed on Aug. 10, 2018.

(51) Int. Cl.
| | |
|---|---|
| *A61K 31/736* | (2006.01) |
| *A61K 31/718* | (2006.01) |
| *A61K 31/729* | (2006.01) |
| *A61K 31/731* | (2006.01) |
| *A61K 31/732* | (2006.01) |
| *A61K 31/734* | (2006.01) |
| *A61P 3/06* | (2006.01) |

(52) U.S. Cl.
CPC .......... *A61K 31/736* (2013.01); *A61K 31/718* (2013.01); *A61K 31/729* (2013.01); *A61K 31/731* (2013.01); *A61K 31/732* (2013.01); *A61K 31/734* (2013.01); *A61P 3/06* (2018.01)

(58) Field of Classification Search
CPC .. A61K 31/731; A61K 31/729; A61K 31/734; A61P 3/04; A61P 3/06
See application file for complete search history.

(56) References Cited

U.S. PATENT DOCUMENTS

| | | | |
|---|---|---|---|
| 4,781,838 A | 11/1988 | Crassous et al. | |
| 5,409,703 A | 4/1995 | McAnalley et al. | |
| 5,545,414 A | 8/1996 | Behr et al. | |
| 6,271,278 B1 | 8/2001 | Park et al. | |
| 7,157,431 B2 | 1/2007 | McAnalley et al. | |
| 8,128,977 B2 | 3/2012 | Anfinsen et al. | |
| 8,465,785 B2 | 6/2013 | Anfinsen et al. | |
| 8,859,701 B2 | 10/2014 | Loick et al. | |
| 9,457,048 B2 | 10/2016 | Davis et al. | |
| 9,492,473 B2 | 11/2016 | Von Maltzahn et al. | |
| 9,855,294 B2 | 1/2018 | Heshmati et al. | |
| 9,867,847 B2 | 1/2018 | Davis et al. | |
| 9,901,595 B2 | 2/2018 | Von Maltzahn et al. | |
| 10,272,155 B2 | 4/2019 | Elenko et al. | |
| 10,584,183 B2 | 3/2020 | Sannino et al. | |
| 10,695,363 B2 | 6/2020 | Rescigno et al. | |
| 10,953,038 B2 | 3/2021 | Heshmati et al. | |
| 2003/0224022 A1 | 12/2003 | Nussunovitch | |
| 2005/0118326 A1 | 6/2005 | Anfinsen et al. | |
| 2005/0250734 A1 | 11/2005 | Moreyra et al. | |
| 2006/0093720 A1 | 5/2006 | Tatz | |
| 2007/0104754 A1* | 5/2007 | Sterling | A61F 2/04 424/423 |
| 2012/0052151 A1 | 3/2012 | Sannino et al. | |
| 2014/0276330 A1 | 9/2014 | Costa | |
| 2015/0125568 A1* | 5/2015 | James | A23L 33/11 426/615 |
| 2015/0196641 A1 | 7/2015 | Elenko et al. | |
| 2015/0282510 A1 | 10/2015 | Makita et al. | |
| 2015/0366898 A1 | 12/2015 | Heshmati et al. | |
| 2015/0366989 A1 | 12/2015 | Liang et al. | |
| 2016/0113953 A1 | 4/2016 | Gannedahl | |
| 2016/0361351 A1 | 12/2016 | Davis et al. | |
| 2017/0319616 A1* | 11/2017 | Lim | A61P 3/04 |
| 2018/0289043 A1 | 10/2018 | Sannino et al. | |
| 2019/0290675 A1 | 9/2019 | Gibson et al. | |
| 2019/0373939 A1 | 12/2019 | Liu | |
| 2020/0009168 A1 | 1/2020 | Von Maltzahn et al. | |
| 2020/0054572 A1* | 2/2020 | Matthiasson | A21D 13/06 |
| 2020/0165406 A1 | 5/2020 | Fitzpatrick et al. | |
| 2021/0000896 A1 | 1/2021 | Mazoyer et al. | |
| 2021/0038871 A1 | 2/2021 | Zhao et al. | |
| 2021/0113596 A1 | 4/2021 | Von Maltzahn et al. | |

FOREIGN PATENT DOCUMENTS

| | | |
|---|---|---|
| WO | 2004/022074 A1 | 3/2004 |
| WO | 2005/036971 A1 | 4/2005 |
| WO | 2010/059725 A1 | 5/2010 |
| WO | 2015/196054 A1 | 12/2015 |
| WO | 2018/106845 A1 | 6/2018 |

OTHER PUBLICATIONS

Klop (Nutrients 2013, 5, 1218-1240; doi:10.3390/nu5041218).*
United States Patent and Trademark Office; International Search Report and Written Opinion issued in App. No. PCT/US19/46077, dated Nov. 13, 2019; 10 pages.
Ni, et al.; "The Control of Ice Crystal Growth and Effect on Porous Structure of Konjac Glucomannan-Based Aerogels"; International Journal of Biologial Macromolecules, 2016, vol. 92, pp. 1130-1135.

(Continued)

*Primary Examiner* — Pancham Bakshi
(74) *Attorney, Agent, or Firm* — Lin Yu; Juniv LLP

(57) ABSTRACT

Methods for reducing cholesterol in a subject can include: providing a superabsorbent material that includes a porous network structure formed from a mixture of a plurality of water soluble polysaccharides that are not chemically cross-linked together; and administering the superabsorbent material to a subject in an effective amount to reduce cholesterol in the subject. The reduction of cholesterol includes at least one of: reducing total cholesterol of the subject; reducing a rate of total cholesterol increase in the subject; or increasing a rate of total cholesterol decrease in the subject. The reduction of cholesterol includes at least one of: reducing cholesterol intake into the subject; reducing cholesterol absorption by the gut of the subject; or absorbing cholesterol material from the gut of the subject into the superabsorbent material. The reduction of cholesterol is by reduction of low-density-lipoprotein cholesterol or high-density-lipoprotein cholesterol.

31 Claims, 6 Drawing Sheets

(56) References Cited

OTHER PUBLICATIONS

Takei, et al.; "Autoclavable Physically-Crosslinked Chitosan Cryogel as a Wound Dressing"; Journal of Bioscience and Bioengineering; 2017; vol. 125; No. 4; pp. 490-495.

Silverstri et al.; "Gelesis Superabsorbent Hydrogel Prevents Hepatic Steatosis and Insulin Resistance in High Fat Diet—Induced NAFLD Pre-Clinical Model"; Humanitas Research Hospital Poster presented at EASL International Liver Congress 2019; Vienna Austria; Apr. 10, 2019; 1 page.

Gelesis; "Gelesis Prevents Pre-Clinical Data Suggesting Proprietary Hydrogel (GS300 Prototype) Reverses the Damage to the Intestines Induced by a High Fat Diet"; website located at: https://www.gelesis.com/2020/11/13/gelesis-presents-pre-clinical-data-suggesting-proprietary-hydrogel-gs300-prototype-reverses-the-damage-to-the-intestines-induced-by-a-high-fat-diet/; Nov. 13, 2020.

Silvestri, Alessandra & Sannino, Alessandro & Vitale, Milena & Mouries, Juliette & Spadoni, Ilaria & Demitri, Christian & Chiquette, Elaine & Rescigno, Maria. (2019). LBP-33-Gelesis superabsorbent hydrogel prevents hepatic steatosis in a high fat diet-induced NAFLD pre-clinical model. Journal of Hepatology. 70. Abstract. 10.1016/S0618-8278(19) 30278-6; 4 pages.

Puretech Health; "Puretech Big—Gelesis (Proprietary Hydrogel Technology) (PLENITY, Gelesis200, GS300, GS400, GS500)"; webpage; located at: https://puretech.red-hill.com/puretech-pipeline/details/hydrogel-platform-technology-for-gi-related-diseases; accessed on May 19, 2021; 3 pages.

Albillos, Agustin & De Gottardi, Andrea & Rescigno, Maria. (2019). The gut-liver axis in liver disease: Pathophysiological basis for therapy. Journal of Hepatology. 72. 10.1016/j.jhep.2019.10.003.

Guo A, Gu J, Wang X, Zhang R, Yin Y, Sun W, Tuo X, Zhang L.; "Effects of superabsorbent polymers on the abundances of antibiotic resistance genes, mobile genetic elements, and the bacterial community during swine manure composting"; Bioresour Technol. Nov. 2017; 244(Pt 1): Abstract; doi: 10.1016/j.biortech.2017.08.016; Epub Aug. 5, 2017; PMID: 28813691; 2 pages.

Liu, X., Steiger, C., Lin, S et al.; "Ingestible hydrogel device"; Nature Communications 10, 493 (2019); https://doi.org/10.1038/s41467-019-08355-2; 10 pages.

Bu et al.; "The hydration mechanism and hydrogen bonding structure of 6-carboxylate chitooligosaccharides superabsorbent material prepared by laccase/TEMPO oxidation system"; Carbohydrate Polymers; vol. 188; Abstract; 2018; ISSN 0144-8617; 1 page.

Liu, X., Steiger, C., Lin, S et al.; "Ingestible hydrogel device"; Nature Communications 10, 493 (2019); https://doi.org/10.1038/s41467-019-08355-2; 31 pages.

Puretech Health; "Puretech Big—Giving Life to Science"; webpage; located at: https://puretechhealth.com/programs/details/gelesis-product-candidates; accessed on May 20, 2021; 4 pages.

Medtech Insight—Informa Pharma Intelligence; "Gelesis 100 Reduces Insulin Resistance in GLOW Obesity Trial"; Webpage; located at: https://medtech.pharmaintelligence.informa.com/MT124859/Gelesis100-Reduces-Insulin-Resistance-in-GLOW-Obesity-Trial; Mar. 29, 2019; 1 page.

\* cited by examiner

METHODS FOR REDUCING CHOLESTEROL WITH SUPERABSORBENT MATERIALS

CROSS-REFERENCE TO RELATED APPLICATIONS

This patent application is a continuation-in-part of U.S. patent application Ser. No. 16/807,004 filed Mar. 2, 2020, which is a continuation of International Patent Application No. PCT/US2019/046077 filed Aug. 10, 2019, which claims the benefit of U.S. Provisional Patent Application No. 62/717,644 filed Aug. 10, 2018, wherein each application is incorporated herein by specific reference in its entirety.

BACKGROUND

Field

The present disclosure relates to use of superabsorbent materials to reduce cholesterol and lipids in a subject.

Description of Related Art

Previously, obesity has been identified as a significant health concern in the modern era. The link between obesity and high fats and cholesterol is well established. Intake of fatty substances, which contribute to increased lipids and cholesterol, at a higher rate than can be excreted lead to increased fatty deposits and increased weight. When the overconsumption of high calories and/or highly fatty foods continues, obesity is a likely result. With the improvement of living standards, the increasing pace of life style, and at the same time reduction of exercise and irregular diet (e.g., high sugar, high calorie, high fat), the obese or overweight population is increasing at an alarming pace. A study recently published by The New England Journal of Medicine projected that 57.3% of today's children will be obese by age 35. Such a bleak prediction highlights the devastating health problem of obesity. Obesity is a major social and economic burden worldwide, accounting for two trillion dollars per year spent on healthcare of obesity-related diseases. Obesity is the underlying cause of many medical complications, such as diabetes, high blood pressure, high cholesterol and various cardiovascular and cerebrovascular diseases. The health risk of obesity is now well recognized, and as a major means to fight obesity, weight control by healthy diet and exercise has received widespread attention. Extensive research suggests that high-carbohydrate and high-fat diets are the main causes of obesity. When the consumed food contains too many calories, the body takes in more calories than it normally uses, and the excess calories will be stored in the form of fat, thereby leading to obesity. Thus, controlling the amount of food calorie intake is a key strategy in weight control.

There are various types of products on the market for reducing lipids and/or cholesterol. The use of crosslinked carboxymethylcellulose as an absorbent member for use in the GI tract to reduce glucose trafficking and providing a bulk hindrance, which can be used for treating obesity (U.S. Pat. No. 10,584,183). The crosslinked carboxymethyl cellulose strategy has also been used to improve glycemic control, which can inhibit lipids and fatty deposits by inhibiting intake of carbohydrate, fat, and protein (U.S. Nos. 10,953,038 and 9,855,294). The use of crosslinked polyvinyl alcohol has also been used for separating lipoproteins from body fluids (U.S. Pat. No. 4,781,838). The use of soluble fibers and cholesterol biosynthesis inhibitors have been disclosed (U.S. No. 2005/0250734), however, this requires an active drug-like compound in the cholesterol biosynthesis inhibitor. The reduction of lipoprotein and cholesterol in the body has also been described with polysaccharides (U.S. Pat. No. 5,408,703).

While there have been proposed treatments for reducing cholesterol, high cholesterol continues to problematically increase. Accordingly, there is still a need in the art to develop an improved dietary product that can be used in a treatment for reducing cholesterol.

SUMMARY

In some embodiments, a method for reducing cholesterol in a subject can include: providing a superabsorbent material that includes a porous network structure formed from a mixture of a plurality of water soluble polysaccharides that are not chemically crosslinked together; and administering the superabsorbent material to a subject in an effective amount to reduce cholesterol in the subject. In some aspects, the reduction of cholesterol includes at least one of: reducing total cholesterol of the subject; reducing a rate of total cholesterol increase in the subject; or increasing a rate of total cholesterol decrease in the subject. In some aspects, the reduction of cholesterol includes at least one of: reducing cholesterol intake into the subject; reducing cholesterol absorption by the gut of the subject; or absorbing cholesterol material from the gut of the subject into the superabsorbent material. In some aspects, the reduction of cholesterol is by reduction of low-density-lipoprotein cholesterol. In some aspects, the reduction of cholesterol is by reduction of high-density-lipoprotein cholesterol.

In some embodiments, the method of reducing cholesterol can include administering the superabsorbent material so that the subject has a slower rate of cholesterol gain. The slower rate of cholesterol gain after the treatment is compared to the subject having a higher rate of cholesterol gain prior to being administered the superabsorbent material. In some aspects, the subject has a high fat diet prior to being administered the superabsorbent material.

In some embodiments, a method for reducing circulating lipid in a subject can include: providing a superabsorbent material that includes a porous network structure formed from a mixture of a plurality of water soluble polysaccharides that are not chemically crosslinked together; and administering the superabsorbent material to a subject in an effective amount to reduce circulating lipid in the subject. In some aspects, the reduction of circulating lipid includes at least one of: reducing amount of circulating lipid of the subject; reducing rate of circulating lipid increase in the subject; or increasing rate of circulating lipid decrease in the subject. In some aspects, the reduction of circulating lipid is reduction of low-density-lipoprotein. In some aspects, the reduction of circulating lipid is reduction of high-density-lipoprotein.

In some embodiments, the method of reducing circulating lipid can include administering the superabsorbent material so that the subject has a slower rate of circulating lipid gain. The slower rate of lipid gain is compared to the subject having a higher rate of circulating lipid gain prior to being administered the superabsorbent material. In some aspects, the subject has a high fat diet prior to being administered the superabsorbent material.

In some embodiments, the reduction of circulating lipid includes a reduction of circulating lipoprotein by at least one of: reducing amount of circulating lipoprotein of the subject; reducing rate of circulating lipoprotein increase in the subject; or increasing rate of circulating lipoprotein decrease in the subject. In some aspects, the lipoprotein is low-density-lipoprotein cholesterol. In some aspects, the lipoprotein is high-density-lipoprotein cholesterol.

In some embodiments, the methods include administering the superabsorbent material so that the subject has a slower rate of circulating lipoprotein gain. The slower rate of circulating lipoprotein gain is compared to the subject having a higher rate of circulating lipoprotein gain prior to being administered the superabsorbent material. The lipoprotein that is reduced can be low-density-lipoprotein cholesterol or high-density-lipoprotein cholesterol.

In some embodiments, a kit can be provided for reducing cholesterol in a subject. The kit can include a container having a superabsorbent material that includes a porous network structure formed from a mixture of a plurality of water soluble polysaccharides that are not chemically cross-linked together. Additionally, the kit can include instructions for a subject to consume the superabsorbent material in an effective amount to reduce cholesterol in the subject. The cholesterol can be low-density-lipoprotein cholesterol or high-density-lipoprotein cholesterol.

In some embodiments, the plurality of water soluble polysaccharides includes at least two of agar, konjac gum, carrageenan, locust bean gum, xanthan gum, tamarind seed gum, guar gum carrageenan, alginate, pectin, gellan gum, chitosan, Arabic gum, and a soluble starch.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

Figure 1:
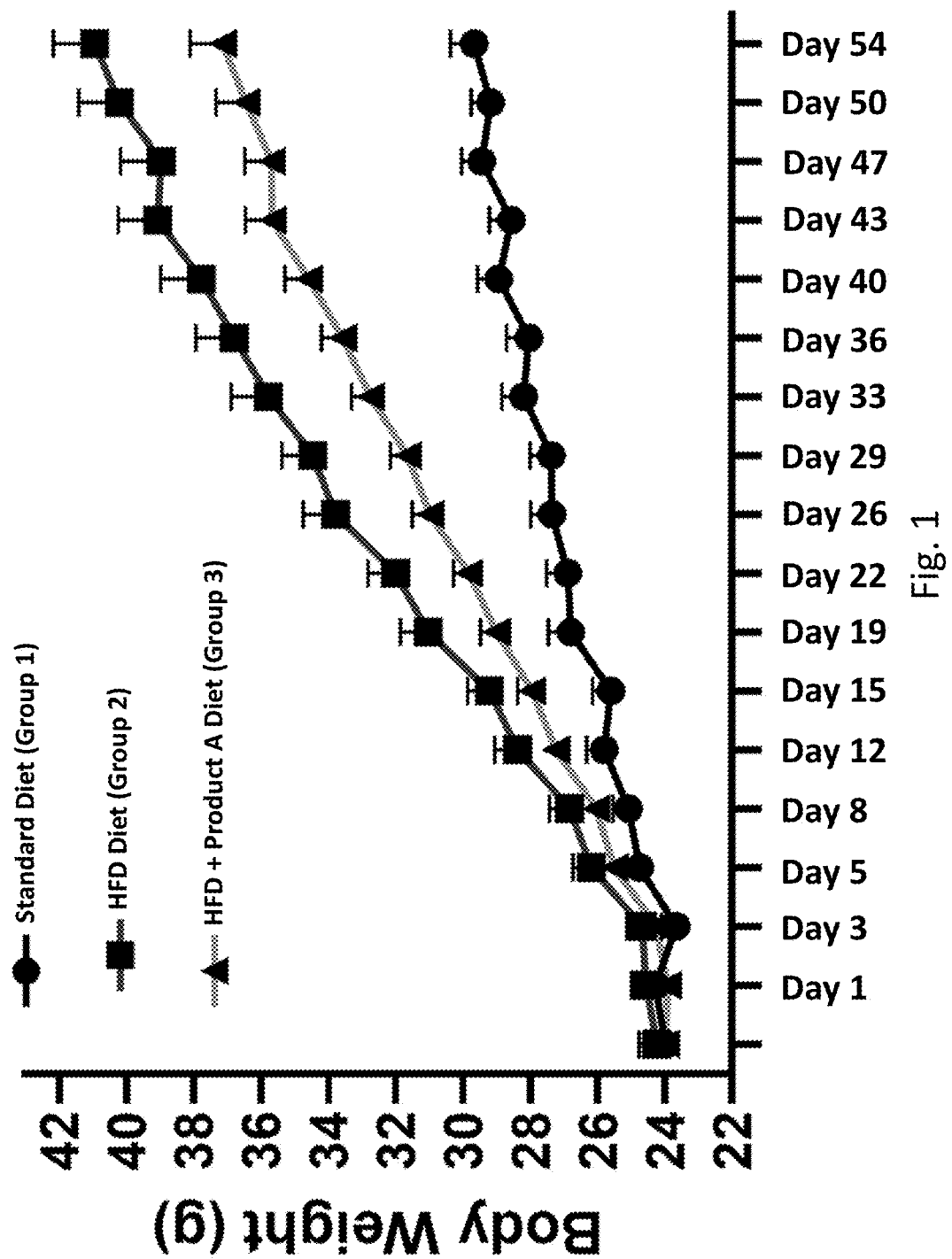
FIG. 1. includes a graph of data that shows the body-weight in grams per day for the mice in the study, where the mice are in groups based on the diets: (Group 1) Standard Diet (e.g., standard rodent chew diet), (Group 2) High-fat Diet (HFD), and (Group 3) High-fat Diet-Treatment 1 (HFD+Product A).

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present technology is directed to the fields of pharmaceutical science, nutritional science, and clinical medicine. Various embodiments relate generally to methods and compositions for the prevention, mitigation, or treatment of diseases related to high cholesterol levels and/or high lipid levels and the symptoms and biological effects thereof.

Generally, the present technology is related to the reducing cholesterol and other lipids, such as lipoproteins that carry cholesterol, with a superabsorbent material. The superabsorbent material is configured to have a significant volume expansion once consumed and/or introduced into an aqueous environment. The superabsorbent material can be administered to a subject for the reduction of cholesterol and other lipids (e.g., lipoproteins) in a variety of administration regimens and in a variety of dosage forms. The superabsorbent material can expand in the gastrointestinal tract of the subject in order to provide the reduction of cholesterol and other lipids. The superabsorbent material may reduce, inhibit, prevent, treat or otherwise mitigate susceptibility, onset, development or progression in any disease state and symptoms associated with elevated lipids, such as cholesterol, which can be considered as total cholesterol or as in LDL-cholesterol or HDL-cholesterol.

Cholesterol is a type of blood fat, and blood fats are commonly known as lipids. Cholesterol and other lipids, such as those that carry cholesterol, are carried in the blood attached to proteins, which form spheres referred to as lipoproteins. So, lipoproteins are lipids attached to proteins, which carry cholesterol in the blood. The lipid part of lipoproteins includes a core of highly hydrophobic polyunsaturated fatty acid (e.g., linoleate) with triglycerides and other fats. There are usually many esterified and unesterified cholesterol molecules in the core. The core can be surrounded by a shell of phospholipids and unesterified cholesterol. The lipoprotein includes a single apolipoprotein B-100 molecule. LDL particles are approximately 22 nm to 27.5 nm in diameter and have a mass of about 3 million daltons on average. With a size ranging from 5 to 17 nm, HDL is the smallest of the lipoprotein particles. It is the densest because it contains the highest proportion of protein to lipids. The following chart provides a guideline for total cholesterol levels in humans associated with risk levels for hypercholesterolemia associated with disease, such as heart disease, often associated with obesity. Accordingly, it can be clearly beneficial to reduce total cholesterol.

| Level | | |
|---|---|---|
| mg/dL | mmol/L | Interpretation |
| <200 | <5.2 | Desirable level (lower risk) |
| 200-240 | 5.2-6.2 | Borderline high risk |
| >240 | >6.2 | High risk |

Accordingly, the treatments of the present technology that can be performed with administered superabsorbent material can be for subjects with a total cholesterol of greater than 200 mg/dl (moderate risk), especially for greater than 240 mg/dl (high risk). The prophylactic use of the superabsorbent material can be for subjects with a normal total cholesterol range; however, it is possible that a subject in the underweight range could desire a prophylactic against developing high cholesterol or a disease associated therewith (e.g., obesity). Accordingly, the superabsorbent material can be provided as a treatment against obesity for any subject, especially as a prophylactic against high cholesterol. In some aspects, the superabsorbent material is provided in an effective amount as a prophylactic to inhibit progression of total cholesterol gain in the subject.

Traditionally, LDL is considered the "bad" lipoprotein or cholesterol (e.g., notably it has the same cholesterol) due to high levels of LDL being associated with cardiovascular diseases and obesity. The following chart shows the recent 2004 guidelines from the American Heart Association, NIH, and NCEP for fasting LDL-cholesterol levels.

| Level mg/dL | Level mmol/L | Standard |
|---|---|---|
| <70 | <1.8 | Optimal LDL cholesterol, corresponding to lower rates of progression of cardiovascular disease, promoted as a target option for those known to clearly have advanced symptomatic cardiovascular disease |
| <100 | <2.6 | Optimal LDL cholesterol, corresponding to lower, but not zero, rates for symptomatic cardiovascular disease events |
| 100-129 | 2.6-3.3 | Near optimal LDL level, corresponding to higher rates for developing symptomatic cardiovascular disease events |
| 130-159 | 3.3-4.1 | Borderline high LDL level, corresponding to even higher rates for developing symptomatic cardiovascular disease events |
| 160-199 | 4.1-4.9 | High LDL level, corresponding to much higher rates for developing symptomatic cardiovascular disease events |
| >200 | >4.9 | Very high LDL level, corresponding to highest increased rates of symptomatic cardiovascular disease events |

Accordingly, the treatments of the present technology that can be performed with administered superabsorbent material can be for subjects with a LDL-C of greater than 100 mg/dl (moderate risk), especially for greater than 130 mg/dl (borderline high risk) or greater than 160 mg/dl (high risk), and even more so when greater than 200 mg/dl (very high risk). The prophylactic use of the superabsorbent material can be for subjects with a normal total LDL-C range (less than 100 mg/dl, and preferably less than 70 mg/dl); however, it is possible that a subject in the underweight range could desire a prophylactic against developing high cholesterol or a disease associated therewith (e.g., obesity). Accordingly, the superabsorbent material can be provided as a treatment against obesity for any subject, especially as a prophylactic against high cholesterol. In some aspects, the superabsorbent material is provided in an effective amount as a prophylactic to inhibit progression of total cholesterol gain in the subject.

Cholesterol levels are commonly identified during health assessments, such as when monitoring obesity. High cholesterol has been linked to obesity. However, not only is total cholesterol high in obese people, the blood cholesterol panel changes in obesity to high LDL and low HDL. These change in obesity bold cholesterol has been linked to increased risks of other diseases, such as heart disease, heart attack, and stroke. Accordingly reducing cholesterol and other lipids is a strategy for reducing obesity.

Obesity is defined by the Centers for Disease Control and Prevention as a weight that is higher than what is considered as a healthy weight for a given height, which can be expressed in terms of being overweight. As used herein, a subject that is overweight is considered to have pre-obesity, or may be considered as having developing obesity. Body Mass Index (BMI) is used as a screening tool for obesity.

Body Mass Index (BMI) can be calculated by a person's weight in kilograms divided by the square of height in meters. A high BMI can be an indicator of high body fatness. Tables can also be obtained that relate body weight (pounds) to height (inches) to give a BMI number. The BMI number indicates the following: BMI less than 18.5 falls within the underweight range; BMI 18.5 to <25 falls within the normal range; BMI 25.0 to <30 falls within the overweight range; and BMI 30.0 or higher falls within the obesity range. Obesity is frequently subdivided into categories: Class 1: BMI of 30 to <35; Class 2: BMI of 35 to <40; and Class 3: BMI of 40 or higher. Class 3 obesity is sometimes categorized as "extreme" or "severe" obesity.

In some embodiments, the superabsorbent material is administered in an effective amount to reduce cholesterol in the subject, wherein the subject is obese.

Accordingly, the treatments of the present technology to reduce cholesterol and other lipids can be performed with administered superabsorbent material for subjects with a BMI of 25.0 for the reduction of weight or treatment of obesity. The prophylactic use of the superabsorbent material to inhibit increases in cholesterol can be for subjects with a normal weight range; however, it is possible that a subject in the underweight range could desire a prophylactic against developing high cholesterol. Accordingly, the superabsorbent material can be provided as a treatment against the subject developing high cholesterol for any subject, especially as a prophylactic. In some aspects, the superabsorbent material is provided in an effective amount as a prophylactic to inhibit progression of cholesterol gains in the subject, wherein the subject is selected from: not obese; developing obesity; obese (Class 1 or Class 2); or morbidly obese (e.g., extreme or severe obesity—Class 3). While subjects are commonly humans, a subject may also be any animal that is capable of becoming being obese, where mammals like mice, rats, cats, dogs, pigs, goats, cows, horses, or others that may also be veterinary subjects.

In some embodiments, a treatment for reducing cholesterol and other lipids can include providing a superabsorbent material for use in the treatment. The superabsorbent material can include porous network structure formed from a mixture of a plurality of water soluble polysaccharides that are not chemically crosslinked together. That is, the polysaccharides are not chemically attached to each other or linked together with any chemical linker. The polysaccharides are separate strands from each other. The polysaccharides are associated during a heating and freezing process to form a network of interconnected polysaccharides. The superabsorbent material can be administered to a subject in an effective amount to provide a treatment for reducing cholesterol in the subject. The treatment for reducing cholesterol can be determined by monitoring the amount of cholesterol in a subject, and identifying reduction of cholesterol amount as well as reduction of characteristics related to cholesterol or reduction in rate of increase in total cholesterol. As such, a subject that is obese may perform the treatment in order to reduce their high cholesterol. Also, a subject that may be developing high cholesterol or even worried about developing high cholesterol can perform the treatment by administration of the superabsorbent material as a prophylactic. The treatment can inhibit the onset or progression of cholesterol gains in a subject when the superabsorbent material is administered to a pre-obese subject. A subject that is not obese or developing obesity may also perform the treatment as a prophylactic measure in an attempt to stop onset of cholesterol gains, or inhibit development of obesity due to high cholesterol.

In some embodiments, provided herein is a method of preventing or treating a disease or condition associated with high cholesterol, such as from high caloric consumption. The method comprises orally administering to a subject suffering from or at an elevated risk of a disease or condition associated with high cholesterol, such as from high caloric consumption, an effective amount of the superabsorbent material.

In another aspect, provided herein is a method of suppressing appetite, enhancing satiety, or lowering calorie intake in a subject, which can be used for reducing cholesterol. The method comprises orally administering to a subject in need thereof an effective amount of the superabsorbent material. The superabsorbent material can be in the dietary composition or used in a volumetrics diet (described herein).

In some embodiments, the treatment includes reducing the cholesterol of the subject. This can include administering the superabsorbent material in an amount effective to reduce the subject's cholesterol. For example, the subject can have an initial cholesterol level (e.g., total cholesterol) prior to receiving the superabsorbent material, and subsequently during and/or after the treatment the subject can have a cholesterol level that is lower than the initial cholesterol. The subject can weight themselves during the treatment to track their cholesterol to determine cholesterol loss from an initial cholesterol. The cholesterol loss can also be tracked along sequential timepoints, which can provide a profile of weight loss for the subject.

In some embodiments, the treatment includes reducing the rate of cholesterol gain in the subject. A subject may have a period of cholesterol increase where they are trending toward obesity or more severe obesity at a higher cholesterol level. The subject can then perform the treatment with the superabsorbent material in order to slow down the rate of cholesterol gain. For example, the subject may have a cholesterol gain rate of 5 mg/dl every 2 months before the treatment, and then have a reduced weight gain rate of 4 or less mg/dl every 2 months. It is important to note that any reduction in rate of cholesterol gain can be beneficial to a subject.

In some embodiments, the treatment includes promoting or otherwise increasing rate of cholesterol loss in the subject. A subject may have a period where they are actively losing cholesterol, whether with the superabsorbent material alone or with a change in lifestyle. For example, the subject may change from an unhealthy lifestyle (e.g., poor eating, high calorie, high fat foodstuffs, etc.) to eating healthy (e.g., portion control, low fat foods, low daily calorie consumption, etc.). The trend toward a healthy lifestyle may induce cholesterol loss. Additionally, the combined use of the superabsorbent material with an improved lifestyle may promote an increase in rate of cholesterol loss.

In some embodiments, the treatment includes reducing the weight of the subject. This can include administering the superabsorbent material in an amount effective to reduce the subject's weight. For example, the subject can have an initial weight prior to receiving the superabsorbent material, and subsequently during and/or after the treatment the subject can have a weight that is lower than the initial weight. The subject can weight themselves during the treatment to track their weight to determine weight loss from an initial weight. The weight loss can also be tracked along sequential timepoints, which can provide a profile of weight loss for the subject. The loss of weight is related to reduction of cholesterol. Thereby, reducing the cholesterol can reduce the weight of the subject.

In some embodiments, the treatment includes reducing the rate of weight gain in the subject by reducing cholesterol in the subject. A subject may have a period of weight increase where they are trending toward obesity or more severe obesity at a higher weight. The subject can then perform the treatment with the superabsorbent material in order to slow down the rate of weight gain by slowing down the cholesterol gain. For example, the subject may have a weight gain rate of 5 pounds every 2 months before the treatment, and then have a reduced weight gain rate of 4 or less pounds every 2 months. It is important to note that any reduction in rate of weight gain can be beneficial to a subject to reduce cholesterol.

In some embodiments, the treatment includes promoting or otherwise increasing rate of weight loss in the subject. A subject may have a period where they are actively losing weight, whether with the superabsorbent material alone or with a change in lifestyle. For example, the subject may change from an unhealthy lifestyle (e.g., poor eating, high calorie, high fat foodstuffs, etc.) to eating healthy (e.g., portion control, low fat foods, low daily calorie consumption, etc.). The trend toward a healthy lifestyle may induce weight loss. Additionally, the combined use of the superabsorbent material with an improved lifestyle may promote an increase in rate of weight loss by reducing rate of cholesterol loss.

The treatment can include reducing caloric intake into the subject with the superabsorbent material. The superabsorbent material expands significantly when hydrated. As a result, the superabsorbent material may cause the subject to consume less calories or less food overall. The filling or satiety effect of the superabsorbent material can reduce the desire for caloric intake.

The treatment can include reducing caloric absorption by the gut of the subject. The reduction in absorption of caloric material by the gut can be facilitated by the subject consuming less caloric material to be absorbed or the superabsorbent material absorbing nutrients, or some other mechanism of action. It is thought that the reduction of cholesterol achieved with the superabsorbent material may be correlated with reduced caloric consumption.

The treatment can include absorbing caloric material from the gut of the subject into the superabsorbent material. The superabsorbent material is absorbent, and thereby when in the digestive system can absorb substances, such as nutrients or caloric materials (e.g., fat, glucose, etc.). As such, the superabsorbent material may absorb such substances that are then excreted out with the superabsorbent material.

The treatment can include increasing transfer of caloric material from bloodstream into gut. There is known permeation of material (e.g., waste) into the gut for excretion. Often, permeation is promoted by a low concentration region pulling movement of substances to increase concentration in that region. The superabsorbent material can absorb substances from the gut, and thereby cause a low concentration region, which can promote transfer of caloric material into the gut. The material may be transferred from the bloodstream into the gut and then absorbed into the superabsorbent material and excreted out.

In some embodiments, the treatment includes administering the superabsorbent material so that the subject has a slower rate of body weight gain associated with reduced cholesterol. The slower rate can be compared to the subject having a higher rate of body weight gain prior to being administered the superabsorbent material. The superabsorbent material has been shown to slow the rate of body weight gain, such as shown in data provided herein in FIG. 1. The reduction in the rate of weight gain was shown in the mice being treated with the superabsorbent material. In some aspects, the subject has a slower rate of body weight gain when on a high fat diet when administered the superabsorbent material. The slower rate can be compared to the subject having a higher rate of body weight gain when on the high fat diet prior to being administered the superabsorbent material. In some aspects, the subject has a high fat diet prior to being administered the superabsorbent material, and potentially during and after being administered the superabsorbent material.

The treatment can include administering the superabsorbent material in an effective amount to reduce low-density lipoprotein (LDL) in the subject. The superabsorbent material has been shown to reduce LDL-C (LDL-cholesterol), such as shown in the data provided herein in FIG. 2. Obesity increases the amount of LDL-C made by the liver, and decreases clearance of LDL-C from blood. As such, high levels of LDL-C are indicative of obesity, and reducing LDL-C levels can indicate reducing obesity. Accordingly, the administering the superabsorbent material in an effective amount has been shown to inhibit LDL-C from increasing in the subject.

Figure 2:
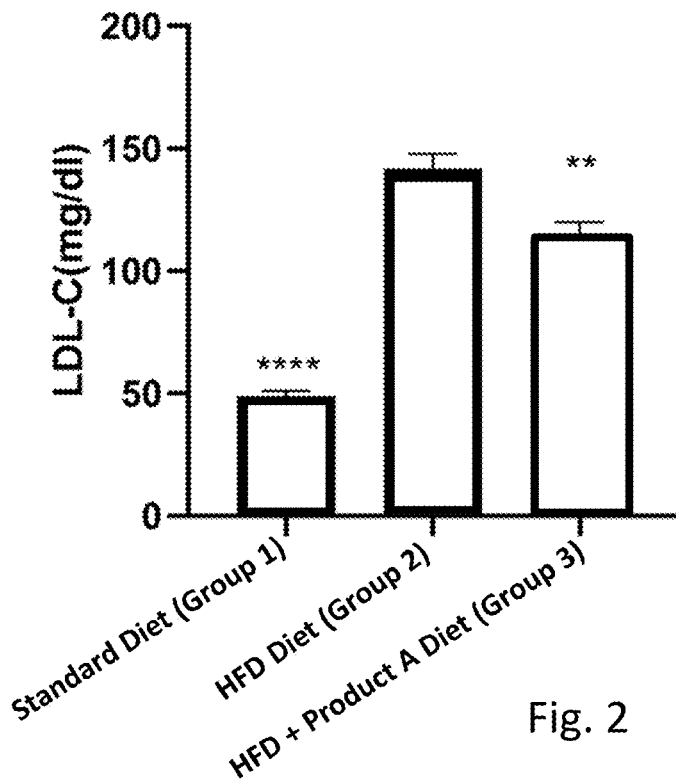
FIG. 2 includes a graph of data that shows the LDL-C levels for Group 1 (standard diet), Group 2 (HFD treatment), and Group 3 (HFD+Product A treatment).
Figure 3:
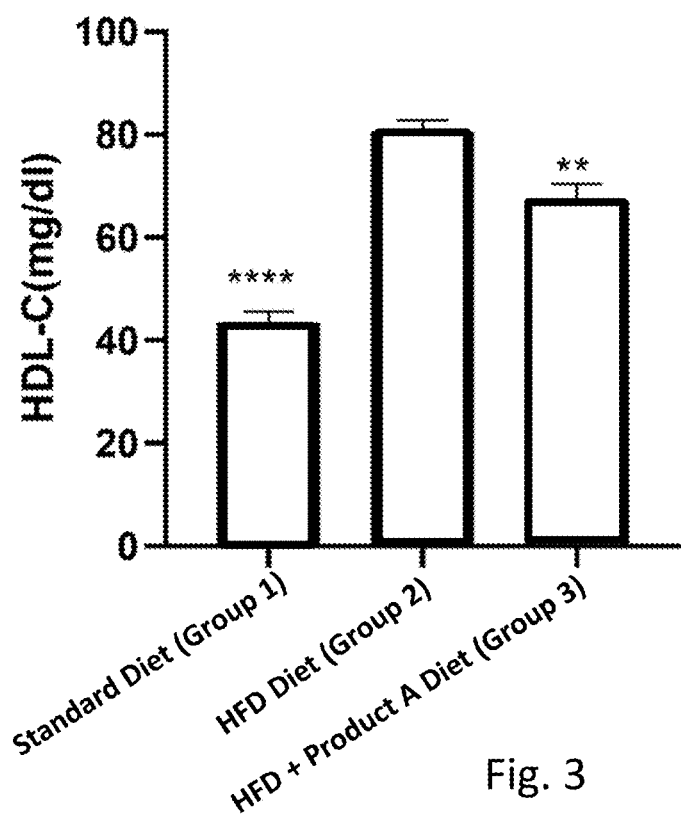
FIG. 3 includes a graph of data that shows the HDL-C levels for Group 1 (standard diet), Group 2 (HFD treatment), and Group 3 (HFD+Product A treatment).

The treatment can include administering the superabsorbent material in an effective amount to reduce high-density lipoprotein (HDL) in the subject. The superabsorbent material has been shown to reduce HDL-C, such as shown in the data provided herein in FIG. 3. HDL is a combination of fat and protein, where the lipids are attached to the protein so that they move through the blood. As such, reduction of HDL-C can be an indication that the superabsorbent material absorbs lipids and/or proteins, and thereby absorbs the HDL. This may be part of reducing total cholesterol. The data showing the reduction of total cholesterol (FIG. 4) combined with the data of FIG. 2 showing reduced LDL-C and FIG. 3 showing reduced HDL-C can indicate that the superabsorbent material reduces overall lipid in the subject and/or reduces overall cholesterol in the subject. Accordingly, the administering the superabsorbent material in an effective amount has been shown to inhibit HDL-C from increasing in the subject. Also, it may inhibit any lipid or cholesterol from increasing in the subject, and attributed to the overall reduction of lipids and cholesterol in the subject.

The treatment can include administering the superabsorbent material in an effective amount to reduce total cholesterol in the subject. The superabsorbent material has been shown to reduce total cholesterol, such as shown in the data provided in FIG. 4. Elevated levels of cholesterol are known to be associated with obesity. As such, reducing levels of total cholesterol can be associated with reducing obesity. The known relationship between cholesterol levels and obesity allows the level of cholesterol to be measured as an indication of obesity level. As a result, reducing total cholesterol may be associated with reducing obesity, and vice versa. Accordingly, the administering the superabsorbent material in an effective amount has been shown to inhibit total cholesterol from increasing in the subject.

Figure 5:
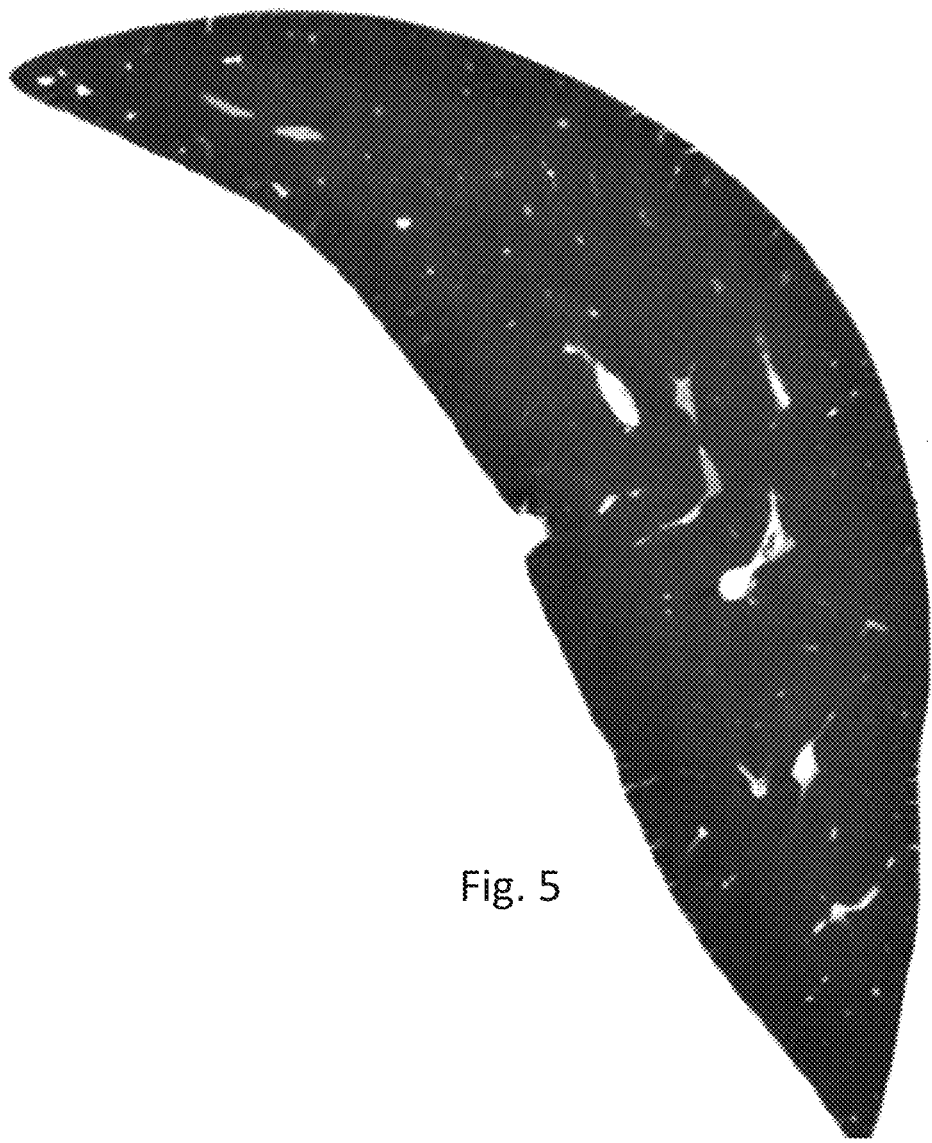
FIG. 5 shows the normal liver under a standard chow diet (Group 1).
Figure 6:
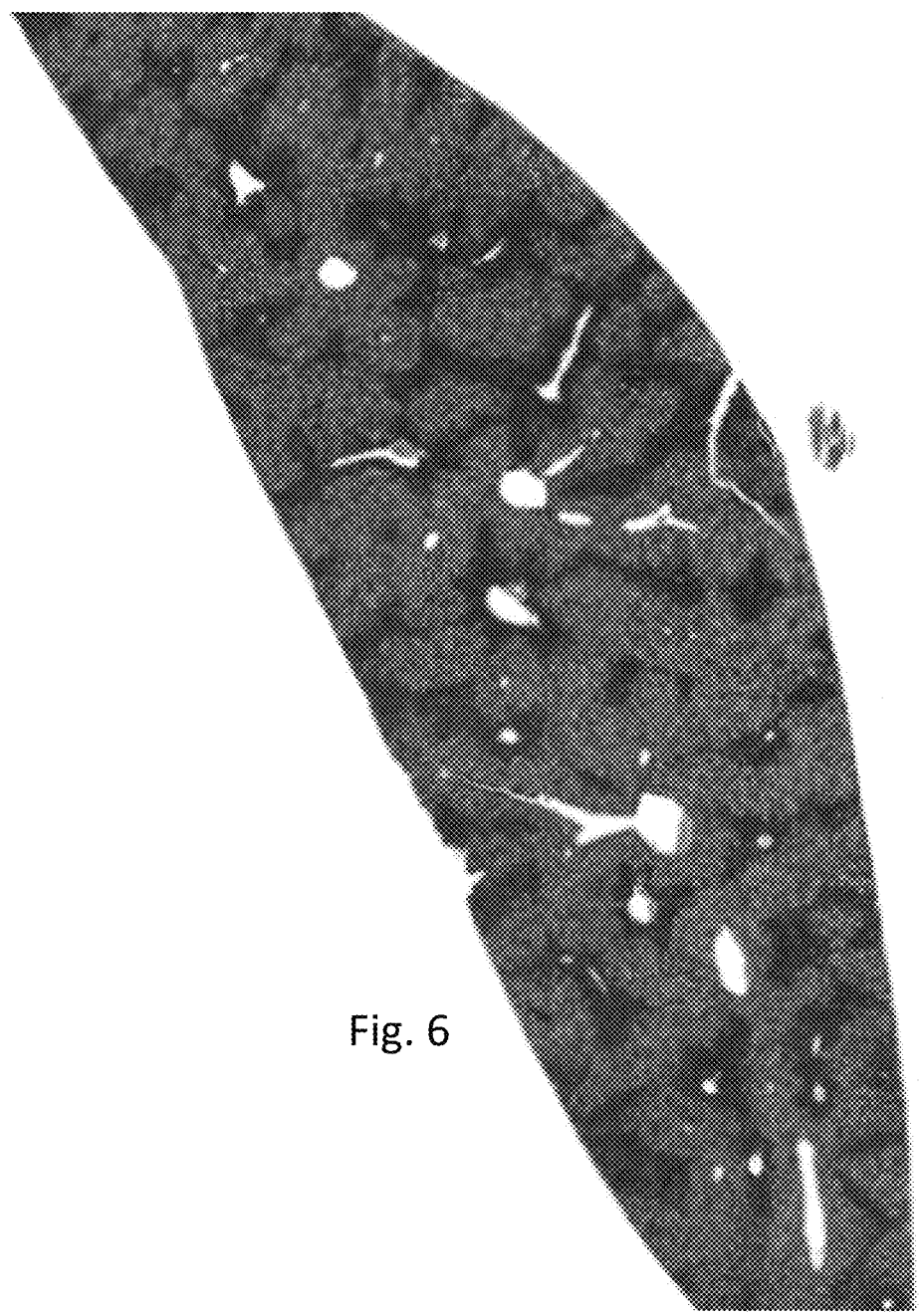
FIG. 6 shows the liver when subjected to the HFD treatment (Group 2).
Figure 7:
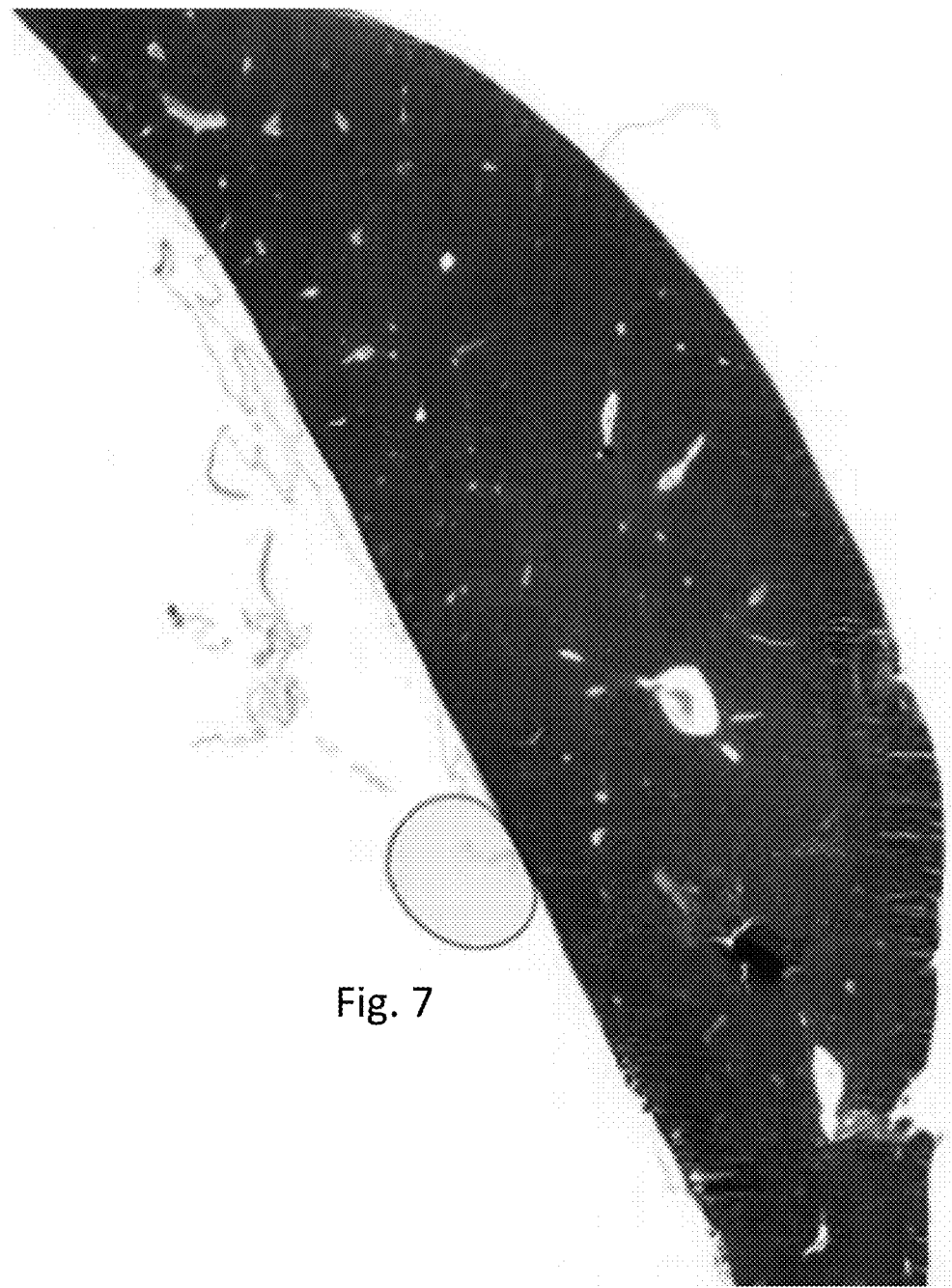
FIG. 7 shows the liver when subjected to the HFD and Product A treatment (Group 3).

The treatment can include administering the superabsorbent material in an effective amount to reduce fat in the subject. The increase of fat is known to occur from increased cholesterol, and any reduction of cholesterol may be attributed to the reduction of fat The superabsorbent material has been shown to reduce fat (e.g., reduce fat in the liver), such as shown in the data provided herein in FIGS. 5, 6, and 7. Accordingly, the administration of the superabsorbent material in an effective amount has been shown to inhibit fat levels, such as those in fatty liver, from increasing in the subject. Increases in cholesterol are associated with increased fatty liver, and thereby reducing cholesterol can reduce fatty liver. The reduced cholesterol inhibits the liver from generating more fat at the liver. While the data shows fat reduction in the liver, the data overall data indicates other organs may have less fat. When the fatty liver data of FIGS. 5, 6, and 7 are combined with FIG. 1, it is reasonable to suggest that the treatment with the superabsorbent material can be used for reducing fat in the subject when cholesterol is reduced.

In some embodiments, the superabsorbent material includes a plurality of water soluble polysaccharides. The plurality of water soluble polysaccharides can include at least two of agar, konjac gum, carrageenan, locust bean gum, xanthan gum, tamarind seed gum and guar gum carrageenan, alginate (such as sodium alginate), pectin, gellan gum, chitosan, Arabic gum, and a soluble starch. In some aspects, the plurality of water soluble polysaccharides includes at least two of agar, konjac gum, and carrageenan, and all three is some instances. In some aspects, the superabsorbent material is administered in a dried and/or powdered form. In some aspects, the superabsorbent material is administered in a hydrated gel form or hydrated liquid form.

In some embodiments, a food composition can be used for the treatment to reduce cholesterol. The food composition can include a high fat diet foodstuff and a superabsorbent material in the foodstuff. The superabsorbent material can be configured as described herein and include a porous network structure formed from a mixture of a plurality of water soluble polysaccharides that are not chemically crosslinked together. The foodstuff can be any consumable composition, but high fat diet food stuffs may be particularly used to include the superabsorbent material. Accordingly, a separate container of superabsorbent material can be provided and added to the food prior to consumption.

In some embodiments, a kit can be provided for a treatment of reducing cholesterol in a subject. The kit can include a superabsorbent material in an administrable form. The administrable form includes the superabsorbent material with a porous network structure formed from a mixture of a plurality of water soluble polysaccharides that are not chemically crosslinked together. The kit also includes instructions for a subject to consume the superabsorbent material in an effective amount to reduce cholesterol. For example, the instructions can include a dosing regimen for daily administration. The administration can be periodic, such as every period of time (e.g., every 4, 6, 8, 10, 12, 24 hours), or discretionary, such as when taken prior to, during or after a meal.

One popular dietary strategy is volumetrics diet, which is the second best diet for weight loss and tied for the fifth best diet overall out of 40 diets evaluated by a panel of health experts in the 2018 U.S. News & World Report's Best Diet Rankings. The main concept of volumetrics diet is to eat natural foods that are low in calories and high in fiber or water such as fruits, vegetables, and soup. Although volumetrics diet has proven to be very effective in weight control and preventing obesity and diabetes, an apparent limitation of this strategy is the diversity of nutrients contained in each food that has high volume and water content but may lack certain essential nutrients. Nevertheless, two key features of volumetrics diet are low calorie density and high-water content. As used herein, the term "calorie density" means the total calories provided per mass unit measure of food. A diet having a low calorie density means that for the same mass or same weight, a low calorie density diet provides less calorie than a regular diet. Accordingly, the superabsorbent material can be administered in the volumetrics diet, such as a supplement (dry, powder) or in foodstuffs (wet, at least partially hydrated). The volumetrics diet can be used to reduce cholesterol.

Superabsorbent Material

In some embodiments, the superabsorbent material is provided as a combination of polysaccharides (e.g., of natural origin or derived therefrom) formulated to have a significant volume expansion. The volume expansion may be induced by absorption of substances, such as body fluids. Aqueous environments can facilitate absorption and expansion by the superabsorbent material.

The superabsorbent material can include agar or carrageenan (e.g., at least 20% (wt %)), and optionally one or more water-soluble natural polysaccharides. In some embodiments, the water-soluble natural polysaccharide includes but is not limited to agar, konjac gum, carrageenan, locust bean gum, xanthan gum, tamarind seed gum and guar gum carrageenan, alginate (such as sodium alginate), pectin, gellan gum, chitosan, Arabic gum, and a soluble starch. The superabsorbent material has a superior swelling capacity (both in terms of water absorption ratio and volume expansion ratio) at room temperature (for example, at a temperature between 15° C. and 25° C.), or at human body temperature (for example, at a temperature between 35° C. and 41° C.), and/or under a neutral pH condition or a human gastric pH condition. In some embodiments, the superabsorbent material disclosed herein has a highly porous structure that is stable and reversible in the drying and rehydration processes under neutral and low pH solutions mimicking human gastric condition. Upon rehydration, the superabsorbent material can expand in volume rapidly (in less than 25 minutes) and maintain a well-defined shape for at least 24 hours under a neutral pH condition or a human gastric pH condition. In some embodiments, the superabsorbent material disclosed herein is stable under an acidic pH such as a gastric pH and maintains the structure and the volume under the acidic gastric pH such that the induced satiety effect in a subject is prolonged.

A variety of water-soluble natural polysaccharides including agar, konjac gum, carrageenan, locust bean gum, xanthan gum, tamarind seed gum, guar gum, etc. are known to possess health benefits as dietary fiber with zero calories (undigestible to human enzymes). Attempts to use these dietary fiber materials to control calorie intake, obesity and other health problems have been made by extensive efforts. However, most of the applications involving the use of these natural polysaccharides materials either do not maintain a certain shape upon rehydration with water or gastric liquid or have poor water absorption and volume expanding capability. Therefore, in previous attempts of use they are cleared by the gastric system quickly and are not very effective in inducing satiety. Now, however, the water-soluble natural polysaccharides can be prepared with the heating and freezing protocol described herein to form the porous structure that is superabsorbent.

In one aspect, provided herein is a superabsorbent material comprising agar, carrageenan, a combination of agar and one or more water-soluble natural polysaccharides, or a combination of carrageenan and one or more water-soluble natural polysaccharides. In some embodiments, the one or more water-soluble natural polysaccharides include but are not limited to agar, konjac gum, carrageenan, locust bean gum, xanthan gum, tamarind seed gum and guar gum carrageenan, alginate (such as sodium alginate), pectin, gellan gum, chitosan, Arabic gum, and a soluble starch. The superabsorbent materials can be obtained by the process disclosed herein.

Disclosed herein are novel superabsorbent materials that are made from water-soluble natural polysaccharides with known health benefits and/or food application qualities (i.e. gelling strength, desirable texture etc.), so the resulting composite natural polysaccharides have the desirable functionalities including but not limited to quick absorbance of a large amount of water upon rehydration with water or gastric liquid at room temperature (around 25° C.) or body temperature (around 37° C.), and quick swelling in volume and maintaining a certain shape and non-aggregated state in water or gastric liquid. The disclosed superabsorbent materials are effective in inducing satiety and have great applications in weight control and preventing or treating other health problems such as obesity.

The disclosed superabsorbent materials comprise an optimized combination of natural polysaccharides (composition ratio and total mass concentration). Upon subjecting to a series of physical treatment that induce and/or enhance the interactions between the natural polysaccharide molecules without using any chemical modifications or crosslinking and dehydration, the superabsorbent materials can form and maintain over a prolonged period of time a porous structure. Any dehydration protocol can be used as long as the drying process can maintain the gel matrix structural without diminishing the water absorption capacity and volume expansion function.

To obtain the disclosed superabsorbent materials, a variety of parameters were tested, including various combination of natural polysaccharides (composition ratio and total mass concentration), and various processing methods were carried out to produce a series of composite natural polysaccharides that have a range of water absorption and volume expanding properties, and shape maintaining (when in contracted or expanded state) properties (e.g., shape may change during expansion from contracted to expanded shape). These natural polysaccharide composite materials with different water absorption, volume expansion and shape stability (when in contracted or expanded state) can be used in a variety of applications. Some examples of the advantages of the disclosed superabsorbent materials and technology are summarized below. By being shape stable, the composition does not deform on its own or otherwise flow from normal gravity.

First, synergistic effects in solution and in gelling process of certain natural polysaccharides can be achieved by the selection of the polysaccharides, the particular ratio range of the selected polysaccharides, and the mass concentration range of the materials. Second, the superabsorbent materials have superior properties in volume expansion and a well-defined shape upon rehydration due to their matrix structure providing enhanced stability and high swelling capacity with respect to absorbent ratio and volume expansion. Unlike conventional technology and materials, the disclosed technology and materials do not use modified or synthetic polymers or chemical crosslinking. As disclosed herein, the gel strength of the materials can be enhanced by freezing treatment of the gel. Finally, since the final product is in a dehydrated form that can be used to absorb water and expand volume to a certain shape upon rehydration, it is important to develop a process that can remove water from the composite gel while maintaining its structural integrity and functionality. Among the many possible dehydration methods that satisfy the aforementioned criteria, disclosed are a thawing-drying method and a freeze-drying method. By thawing-drying, the preformed gel is thawed and then dried at a temperature (e.g. 50-60° C.) without melting the gel structure under atmospheric pressure. By freeze-drying, the preformed gel is directly lyophilized under vacuum. Both methods yield samples with good to great water absorption and volume expansion properties. In some embodiments, the freeze-dried samples have a more porous structure and higher water absorption capacity, while the thawing-dried samples have a more compact structure in the dry state but can resume a porous structure upon rehydration, although its water absorption capacity is lower than that of freeze-dried samples.

There are a wide range of high-quality water-soluble dietary fibers that are non-toxic to human body, low in calories, and cannot be digested and decomposed by gastric acid and enzymes in the human body. These include seaweed polysaccharides, such as agar and carrageenan extracted from marine algae, konjac flour, guar gum, pectin, locust bean gum, tamarind polysaccharide gum, etc. extracted from plants, xanthan gum extracted by microorganism fermentation, microbial polysaccharides such as gellan gum. The superabsorbent material prepared from these natural polysaccharides have the functions of promoting intestinal peristalsis, laxative, detoxification, and preventing intestinal diseases; slowing postprandial blood glucose rise and reducing the risk of diabetes; lowering cholesterol and reducing the risk of cardiovascular and cerebrovascular diseases; and improving the metabolism of neutral fat and lipid and inhibiting body fat accumulation.

Agar is a water-soluble polysaccharide extracted from red algae. At room temperature, agar can absorb water and swell, but it needs to be heated to above 80° C. to dissolve in water. When the agar solution is cooled to 32-42° C., it will start to solidify into gel, and the solidified agar gel needs to be heated to 75° C. or above before it can melt again. Thus, agar is uniquely advantageous in many applications. In addition, compared with other natural gelling agents, agar has self-gelling property, that is, it does not require any additional substance during gelling process. Thus, agar gel is a purely natural product. Further, agar cannot be digested and absorbed by the human body, and therefore is widely used in food, biological applications and medicine.

Carrageenan is another water-soluble polysaccharide extracted from red algae. Based on structural differences, carrageenan is divided into three main classes: Kappa, Iota, and Lambda. K-carrageenan can swell in water at room temperature but can only dissolve in water at a temperature above 70° C. When the carrageenan solution is cooled to 20-25° C., it will start to solidify into gel (or it can form gel at higher temperatures when KCl is added), and the solidified carrageenan gel needs to be heated to 47° C. or above before it can melt again.

Konjac gum (konjac glucomannan, KGM) is derived from Amorphophallus Konjac species, it is a high molecular polysaccharide made of residues of mannose and glucose, linked together by β-1,4 with a molar ratio of 1.6:1.0. It is a slightly branched polysaccharide having a molecular weight of 200,000 to 2,000,000 Daltons (actual molecular weight of KGM depends on the konjac variety).

As described above, certain types of polysaccharide molecules can interact with each other in solution to generate synergistic effect in gelling process. For example, in a mixed solution of agar that also contains carrageenan and konjac gum, when the temperature is increased to above 80° C., the agar molecules and the carrageenan/konjac gum molecules exist in the form of random coils. As the temperature of the solution decreases, the random coils of agar and possibly some carrageenan/konjac gum molecules start to interact with each other and form double helical structures; when the temperature is further reduced, the double helices will further interact with each other and self-assemble; and when the temperature drops to the gelling point, it can form a three-dimensional porous, network structure composed of agar molecules and carrageenan/konjac gum molecules. When the gel is further frozen for an extended period of time, any polysaccharide molecules, in particular carrageenan/konjac gum molecules, that are not incorporated in the gel matrix in the initial gelling step, may be induced to interact with the preformed agar gel network by the cryogelation effect. As a result, a composite material is formed with a highly stable porous structure that is capable of encapsulating a large amount of water molecules. By removing the water molecules while maintaining the three-dimensional porous, network structure, a superabsorbent material can be obtained.

In general, when a high temperature agar is mixed with one or more water-soluble natural polysaccharides, the agar molecules may interact with the other natural polysaccharide molecules as the temperature of the solution decreases. Due to the different molecular structures of the polysaccharides, the interactions between different natural polysaccharide molecules and the agar molecules are different. The resulting three-dimensional porous network structures and properties of the composite materials made from the agar and one or more water-soluble natural polysaccharide molecules are also different. By removing water molecules while maintaining the three-dimensional porous network structure formed by the agar molecules and the one or more natural polysaccharide molecules, a superabsorbent material can be obtained.

In some embodiments, the superabsorbent material comprises at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% (wt %) of agar and/or carrageenan, or any range between any of these values. In some embodiments, the superabsorbent material comprises at least 20% (wt %) of carrageenan. The agar or carrageenan and the one or more water-soluble natural polysaccharides do not form any chemical cross-linkage in the superabsorbent material but rather form strong molecular interactions induced by cryogelation or cryo-structuring to result in a highly porous network structure. The porous network structure is highly stable and reversible in the drying and rehydration processes under neutral and low pH solutions mimicking human gastric condition.

The superabsorbent material has a great swelling capacity at room temperature (for example, at a temperature between 15° C. and 25° C.), or at human body temperature (for example, at a temperature between 35° C. and 41° C.), and under a neutral pH condition or a human gastric pH condition. Upon rehydration, the superabsorbent material can expand in volume rapidly in less than 2 hours, less than 1.5 hours, less than 1 hour, less than 30 minutes or less than 15 minutes (for example, in less than 25 minutes) and maintain a well-defined shape for at least 24 hours, at least 36 hours, or at least 48 hours under a neutral pH condition or a human gastric pH condition. In some embodiments, upon rehydration, the superabsorbent material can expand in volume rapidly in less than 25 minutes and maintain a well-defined shape for at least 24 hours under a neutral pH condition or a human gastric pH condition.

In some embodiments, the swelling capacity of the superabsorbent materials is measured by absorption ratio calculated by the formula: (the weight of fully rehydrated sample)/(the weight of dry sample). For example, the superabsorbent material disclosed herein has an absorption ratio of at least 10 times or up to 200 times of its own weight in deionized water, or at least 5 times or up to 100 times of its own weight in artificial gastric juice. In some embodiments, the volume expansion capacity of the superabsorbent materials is measured by volume expansion ratio calculated by a formula: the volume of fully rehydrated sample/the volume of dry sample. For example, the superabsorbent material disclosed herein has a volume expansion ratio of at least 5 times or up to 150 times in deionized water, or a volume expansion ratio of at least 5 times to up to 100 times in artificial gastric juice.

In some embodiments, the swelling capacity is represented by absorption ratio measured by the following formula: absorption ratio=(the wet weight of the superabsorbent material swelled in water or a specific buffer to saturation)/(the dry weight of the superabsorbent material), and/or by volume expansion ratio measured by the following formula: volume expansion ratio=(the volume of the fully hydrated superabsorbent material soaked in water or a specific buffer to saturation)/(the volume of the starting dry superabsorbent material). In some embodiments, the absorption ratio and/or the volume expansion ratio is measured at room temperature. In some embodiments, the absorption ratio and/or the volume expansion ratio is measured at about 37° C. In some embodiments, the absorption ratio and/or the volume expansion ratio is measured at a neutral pH. In some embodiments, the absorption ratio and/or the volume expansion ratio is measured at a physiological pH. In some embodiments, the absorption ratio and/or the volume expansion ratio is measured at a gastric pH. In some embodiments, the superabsorbent materials obtained by the process disclosed herein have a water absorption ratio of at least 10 fold, at least 20 fold, at least 30 fold, at least 40 fold, at least 50 fold, at least 60 fold, at least 70 fold, at least 80 fold, at least 90 fold, at least 100 fold, at least 110 fold, at least 120 fold, at least 130 fold, at least 140 fold, at least 150 fold, at least 160 fold, at least 170 fold, at least 180 fold, at least 190 fold, or at least 200 fold of the weight of the dry superabsorbent material before swelling, or within any range between any of these values. In some embodiments, the superabsorbent materials obtained by the process disclosed herein have a gastric fluid absorption ratio of at least 5 fold, at least 10 fold, at least 15 fold, at least 20 fold, at least 25 fold, at least 30 fold, at least 35 fold, at least 40 fold, at least 45 fold, at least 50 fold, at least 60 fold, at least 70 fold, at least 80 fold, at least 90 fold, or at least 100 fold of the weight of the dry superabsorbent material before swelling, or within any range between any of these values. In some embodiments, the superabsorbent materials obtained by the process disclosed herein have a volume expansion ratio in water of at least 10 fold, at least 20 fold, at least 30 fold, at least 40 fold, at least 50 fold, at least 60 fold, at least 70 fold, at least 80 fold, at least 90 fold, at least 100 fold, at least 110 fold, at least 120 fold, at least 130 fold, at least 140 fold, or at least 150 fold of the weight of the dry superabsorbent material before swelling, or within any range between any of these values. In some embodiments, the superabsorbent materials obtained by the process disclosed herein have a volume expansion ratio in gastric fluid of at least 5 fold, at least 10 fold, at least 15 fold, at least 20 fold, at least 25 fold, at least 30 fold, at least 35 fold, at least 40 fold, at least 45 fold, at least 50 fold, at least 60 fold, at least 70 fold, at least 80 fold, at least 90 fold, or at least 100 fold of the weight of the dry superabsorbent material before swelling, or within any range between any of these values.

Disclosed herein is a process of obtaining a superabsorbent material comprising the steps of combining agar and one or more water-soluble natural polysaccharides at various ratio and mass concentrations, heating the mixture in water to completely dissolve the agar and one or more water-soluble natural polysaccharides, and forming a gel by cooling the mixture, and further stabilizing the gel by cryogelation below freezing point. The obtained superabsorbent materials have a highly porous structure and can absorb a large amount of water molecules. Upon dehydration at room or body temperature while maintaining the three-dimensional network structures, the obtained superabsorbent materials can absorb a large amount of water, expand in volume and maintain a well-defined shape at room or body temperature, and under neutral or gastric conditions. Unlike the unprocessed water-soluble natural polysaccharides, which are easily degradable in stomach, the superabsorbent materials disclosed herein can maintain its three-dimensional network structure for a prolonged period even in the gastric environment at human body temperature. In other words, the superabsorbent materials disclosed herein requires higher than the gastric environment temperature (about 37° C.) to be re-dissolved in aqueous solution, thereby effectively overcoming the problem of quick metabolism and dissociation of water-soluble polysaccharides in gastric fluid when used as a weight-loss diet. The superabsorbent materials disclosed herein have superior swelling capacity and water retention properties under physiological conditions in gastric fluid, allowing them wide applications as dietary materials and/or delivery vehicles.

In yet another aspect, provided herein is a method of preparing a superabsorbent material comprising agar, carrageenan, a combination of agar and one or more water-soluble natural polysaccharides, a combination of carrageenan and one or more water-soluble natural polysaccharides, or a combination of agar and carrageenan and one or more water-soluble natural polysaccharides. The method comprises the steps of adding agar, carrageenan, a combination of agar and one or more water-soluble natural polysaccharide, a combination of carrageenan and one or more water-soluble natural polysaccharides, or a combination of agar and carrageenan and one or more water-soluble natural polysaccharides to water to form a mixture, heating the mixture to a temperature of between 80° C. and 100° C. with stirring until the one or more polysaccharides are completely dissolved, allowing the mixture to cool down to between 20° C. and 45° C. to form a gel over a period of 2 to 10 hours, freezing the preformed gel at a temperature below freezing temperature for at least 4 hours, and drying the frozen gel to obtain the superabsorbent material. In some embodiments, the drying step comprises thawing the gel and drying under normal pressure at 50-60° C. ("thawing-dry"). In some embodiments, the drying step comprises directly drying the frozen gel by lyophilization without thawing ("freeze-dry"). In some embodiments, the method further comprises pulverizing the dried gel to obtain the superabsorbent material in a powder form of various mesh sizes.

In another aspect, disclosed herein is a method of preparing a superabsorbent material comprising a combination of agar and one or more water-soluble natural polysaccharides. The method comprises the steps of: adding agar and one or more water-soluble natural polysaccharide, to water to form a mixture, heating the mixture to a temperature of between 80° C. and 100° C. with stirring until the one or more polysaccharides are completely dissolved, allowing the mixture to cool down to between 20° C. and 45° C. to form a gel over a period of 2 to 10 hours (the temperature and time for the gelling step can be optimized depending on materials used), freezing the preformed gel at a temperature below freezing for at least 4 hours (the temperature and time for the cryogelation step can be optimized depending on materials used), and drying the frozen gel to obtain the superabsorbent material by thawing the gel and dry under normal pressure at 50-60° C. (referred to as thawing-dry), or dry the frozen gel by lyophilization (referred to as freeze-dry), or any drying methods that can remove water without damaging the gel matrix structure and diminishing the water absorption capacity and volume expansion function. In some embodiments, the method further comprises pulverizing the dried gel to obtain the superabsorbent material in a powder form of various mesh sizes depending on specific application needs. In some embodiments, the drying step includes freeze-drying or vacuum freeze-drying the frozen gel. In some embodiments, the drying step includes thawing the frozen gel, filtering the thawed gel to obtain a filter cake, and drying the filter cake. The filter cake can be dried by any suitable method, including but not limited to air drying, heat drying, freeze-drying, vacuum drying, or a combination thereof.

The dried gel of any embodiment of superabsorbent material can be further pulverized into a powder form for easy storage and applications. As described herein, during the cooling process the agar and/or carrageen, and one or more natural polysaccharides can form a three-dimensional structure. In some embodiments, a three-dimensional, porous structure is formed as shown by SEM images. After dehydration and swelling, the shape and form of this three-dimensional structure can be maintained. As demonstrated in the working examples, the swelled superabsorbent materials appeared in a non-flowing gel state with a well-defined shape. Thus, the superabsorbent materials obtained by the disclosed process have superior swelling capacity in terms of volume expansion and shape stability and water retention properties.

As demonstrated in the working examples, different samples of the superabsorbent materials showed a wide range of water absorption capacity, suggesting that the composition, molar ratio and concentration can affect the properties of the superabsorbent materials. The disclosed superabsorbent materials are characterized by highly stable and uniform structure, suggesting that molecules of different natural polysaccharides interact with each other to form a new and unique matter, rather than simple physical mixtures of various polymers which would be expected to show heterogeneous structural features. The different composite natural polysaccharide materials made from different compositions, ratio and concentration clearly have different structures, which explain their different functionalities such as water absorption ratio and volume expansion ratio and shape stability. The liquid nitrogen flash freezing followed by lyophilization captured the porous structural features of various composite natural polysaccharides materials.

In a related aspect, provided herein is a superabsorbent material produced by the method described above. The superabsorbent material produced by the disclosed method can be used in food or health supplement industry and/or as delivery vehicle for therapeutic agents and/or nutrients.

The superabsorbent materials disclosed herein have various applications in healthcare and food industries. For example, the superabsorbent material can be used as a medical diet or dietary supplement, which can increase the satiety of the patient thereby to reduce the intake of calories and carbohydrate, which can reduce cholesterol. Such a diet or dietary supplement, when used in combination with a therapy, can enhance the therapeutic effect on obesity and diabetes; and even when used alone, can prevent or delay the onset of certain diseases such as obesity and diabetes, which are related to high cholesterol. In some embodiments, the superabsorbent materials disclosed herein can be used as a vehicle for loading medicine for the preparation of medical materials.

Some examples of the applications of the superabsorbent materials disclosed herein include but are not limited to the following: (1) the superabsorbent materials disclosed herein can be added to a cold or warm liquid diet or a drink such as water, juice, milk, beverage, soup, and pudding for human consumption; (2) the superabsorbent materials disclosed herein can be directly consumed in the form of a powder, a tablet, a capsule or any other suitable form, followed by drinking an appropriate amount of liquid to allow liquid absorption and swelling in the stomach; (3) the superabsorbent materials disclosed herein can be added as an ingredient to various food products such as bread, cakes, biscuits, energy bars and other foods to make low-calorie, dietary fiber-rich functional foods and/or volumetrics diet to induce satiety for a prolonged time. Because the superabsorbent materials disclosed herein can be in dry powder form and has superior swelling capacity, a small amount of consumption (about 5 g to 20 g) can achieve a therapeutic effect. The superabsorbent materials are also stable under normal shipping and storage conditions. Therefore, the superabsorbent materials can also be used as a vehicle to deliver drugs and other nutrients.

In some embodiments, the superabsorbent material can be administered in a dosage in a range from 0.25 g to 750 g, from 0.5 g to 500 g, from 1 g to 100 g, from 10 g, to 90 g, from 20 g to 80 g, 30 g to 70 g, 40 g, to 60 g, or some value therebetween. Low dose superabsorbent material can be considered to be from 0.24 g to 25 g, or 0.5 g to 20 g, from 1 g to 15 g, 5 g to 12 g, 6 g to 10 g, or about 8-9 g per dosage. The dosing can be once, twice, or three times daily, such as with meals.

In another aspect, provided herein is a dietary composition comprising the superabsorbent material described above. In another aspect, provided herein is a volumetrics diet comprising the superabsorbent material or the dietary composition disclosed herein In some embodiments, the superabsorbent material or the dietary composition comprising the superabsorbent material further comprises one or more additional essential nutrients including macronutrients and micronutrients. Such nutrients include but are not limited to a variety of proteins and active peptides, vitamins and trace elements and minerals, and prebiotics.

In some embodiments, the superabsorbent material has a volume expansion ration of at least 5 times or up to 150 times in deionized water. In some embodiments, the superabsorbent material is neither expanded with gas nor digested with an enzyme prior to or during formation of the superabsorbent material.

SUPERABSORBENT MATERIAL EXAMPLES

The observations described in Examples 1-23 can be reviewed in U.S. No. 2020/0197904, which is incorporated herein by specific reference in its entirety.

Example 1: Materials and Methods

Preparation of artificial gastric juice (according to the United States Pharmacopoeia): 2.0 g sodium chloride, 3.2 g pepsin (1500 U/mg), and 7.0 ml of concentrated hydrochloric acid were added to distilled water and the volume was adjusted to 1000 ml.

Absorption ratio test: 1.0 g of a dry superabsorbent material was mixed with 250 g of distilled water in a beaker, and the mixture was allowed to stand for 3 hours at 25° C. Then the sample in the beaker was poured onto a 120-mesh sieve and kept for 1 hour at 25° C. to allow the water to drip off naturally. The wet sample remained on the sieve was recovered and weighed. The absorption ratio was calculated as follows: Absorption ratio=(the weight of the wet sample recovered from the sieve)/(the weight of the starting dry sample).

Similarly, the absorption ratio of a sample superabsorbent material in the artificial gastric juice was tested using the procedure described above. Instead of the distilled water, 1.0 g of the dry sample was mixed with the artificial gastric juice and allowed to stand for 3 hours at 37° C. Then the wet sample was recovered and weighed, and the absorption ratio was calculated as described above.

Gel strength test: 1.5 g of agar was added to 98.5 g of deionized water. The mixture was stirred and heated to 90° C. until the agar was completely dissolved, then cooled to 20° C. to form an agar gel. The gel was allowed to stand for 24 hours before use. 1.5 g of κ-carrageenan was added to 98.3 grams of deionized water. The mixture was stirred and heated to 90° C. until κ-carrageenan was completely dissolved. 0.2 g of potassium chloride was added and then cooled to 20° C. to form a carrageenan gel. The gel was allowed to stand for 24 hours before use. The prepared agar gel and the carrageenan gel were tested for gel strength using a texture analyzer (Stable Micro Systems, TA.XT. Plus Texture Analyser, UK). The test settings were: probe P/0.5, pressing speed 1.5 mm/s, running speed 1.0 mm/s, recovering speed 1.5 mm/s, and the pressing distance was 20 mm. The agar gel and the carrageenan gel used herein had a measured gel strength of 1000 g/cm$^2$ and 1200 g/cm$^2$, respectively.

Viscosity test: 2.0 g of a water-soluble natural polysaccharide was added to 198 g of deionized water. The mixture was stirred at room temperature until the polysaccharide was completely dissolved. The viscosity of the solution was measured at 25° C. using a Brookfield viscometer. The measured viscosity of the starting materials used herein is listed in Table 1 below.

TABLE 1

| Viscosity of Starting Materials | |
| --- | --- |
| Polysaccharide | Viscosity |
| Konjac gum powder aqueous solution | 22000 mpa · s |
| Locust bean gum aqueous solution | 2500 mpa · s |
| Guar gum aqueous solution | 3500 mpa · s |
| Xanthan gum aqueous solution | 3200 mpa · s |
| Tamarind seed gum aqueous solution | 60 mpa · s |

Examples 2-17

The characteristics of all samples from Examples 2-17 are summarized in Table 2 below. These examples were prepared as described with the ingredients and ratios of materials in the preparation condition. The preparation condition included heated mixing, such as temperatures to about 95° C. with stirring until the polysaccharides were completely dissolved, then slowly cooled to form a gel. The gel was kept at 10° C. for 2 hours, and then frozen for 10 hours in a −20° C. freezer to obtain a frozen gel. In some of the examples, direct freeze drying was used with to decrease the water content to 15-18% and pulverizing. In some examples, the frozen gel was thawed and filtered, and the filter cake was dried at 50° C. under the normal pressure to decrease the water content to 15-18% and then pulverized.

TABLE 2

| | | | | | |
| --- | --- | --- | --- | --- | --- |
| Characterization of the Superabsorbent Materials | | | | | |
| Ex.. No. | Samp. No. | Ingredients and ratio | Preparation Condition | Abs. ratio in water | Abs. ratio in gastric juice |
| 2 | 1 | Agar:κ-carrageenan: konjac gum = 1:1:1 | Simple mixture | 4.0 | 2.6 |
| 3 | 2 | Agar:κ-carrageenan: konjac gum = 1:1:1 Dry powder; Non-flowing hydrated gel state. | Superabsorbent material obtained by heated mixing to dissolve, slowly cooled to gel, then frozen for direct freeze drying. | 88.6 | 31.5 |
| 3 | 3 | Agar:κ-carrageenan: konjac gum = 1:1:1 Dry powder; Non-flowing hydrated gel state. | Superabsorbent material obtained by heated mixing to dissolve, slowly cooled to gel, then frozen, then thawed and dried at 50° C. then pulverized. | 97.2 | 34.5 |

TABLE 2-continued

Characterization of the Superabsorbent Materials

| Ex. No. | Samp. No. | Ingredients and ratio | Preparation Condition | Abs. ratio in water | Abs. ratio in gastric juice |
|---|---|---|---|---|---|
| 4 | 4 | Agar:κ-carrageenan:konjac gum = 1:1:2 Dry powder; Non-flowing hydrated gel state. | Superabsorbent material obtained by heated mixing to dissolve, slowly cooled to gel, then frozen for direct freeze drying. | 79.7 | 29.5 |
| 4 | 5 | Agar: κ-carrageenan:konjac gum = 1:1:2 Dry powder; Non-flowing hydrated gel state. | Superabsorbent material obtained by heated mixing to dissolve, slowly cooled to gel, then frozen, then thawed and dried at 50° C. then pulverized. | 95.3 | 34.1 |
| 5 | 6 | Agar:κ-carrageenan:konjac gum = 2:1:1 Dry powder; Non-flowing hydrated gel state. | Superabsorbent material obtained by heated mixing to dissolve, slowly cooled to gel, then frozen for direct freeze drying. | 67.4 | 23.8 |
| 5 | 7 | Agar:κ-carrageenan:konjac gum = 2:1:1 Dry powder; Non-flowing hydrated gel state. | Superabsorbent material obtained by heated mixing to dissolve, slowly cooled to gel, then frozen, then thawed and dried at 50° C. then pulverized. | 68.9 | 26.0 |
| 6 | 8 | Agar:κ-carrageenan:konjac gum = 1:2:1 Dry powder; Non-flowing hydrated gel state. | Superabsorbent material obtained by heated mixing to dissolve, slowly cooled to gel, then frozen for direct freeze drying. | 105.4 | 23.7 |
| 6 | 9 | Agar:κ-carrageenan:konjac gum = 1:2:1 Dry powder; Non-flowing hydrated gel state. | Superabsorbent material obtained by heated mixing to dissolve, slowly cooled to gel, then frozen, then thawed and dried at 50° C. then pulverized. | 121.0 | 27.6 |
| 7 | 10 | Agar:κ-carrageenan:konjac gum = 1:2:1 Dry powder; Non-flowing hydrated gel state. | Superabsorbent material obtained by heated mixing to dissolve, slowly cooled to gel, then frozen for direct freeze drying. | 165.1 | 21.8 |
| 7 | 11 | Agar:κ-carrageenan:konjac gum = 1:2:1 Dry powder; Non-flowing hydrated gel state. | Superabsorbent material obtained by heated mixing to dissolve, slowly cooled to gel, then frozen, then thawed and dried at 50° C. then pulverized. | 195.0 | 26.5 |
| 8 | 12 | Agar:κ-carrageenan:konjac gum = 1:2:1 Dry powder; Non-flowing hydrated gel state. | Superabsorbent material obtained by heated mixing to dissolve, slowly cooled to gel, then frozen, then thawed and dried at 50° C. then pulverized. | 73.2 | 36.0 |
| 9 | 13 | Agar:κ-carrageenan:konjac gum = 1:2:1 Dry powder; Non-flowing hydrated gel state. | Superabsorbent material obtained by heated mixing to dissolve, slowly cooled to gel, then frozen, then thawed and dried at 50° C. then pulverized. | 69.0 | 26.0 |
| 10 | 14 | Agar:κ-carrageenan:locust bean gum = 2:1:1 Dry powder; Non-flowing hydrated gel state. | Superabsorbent material obtained by heated mixing to dissolve, slowly cooled to gel, then frozen, then thawed and dried at 50° C. then pulverized. | 52.0 | 23.8 |
| 11 | 15 | Agar:κ-carrageenan:konjac gum:xanthan gum = 5:5:2:3 Dry powder; Non-flowing hydrated gel state. | Superabsorbent material obtained by heated mixing to dissolve, slowly cooled to gel, then frozen, then thawed and dried at 50° C. then pulverized. | 78.0 | 27.5 |
| 12 | 16 | Agar:κ-carrageenan:tamarind seed gum = 2:2:1 Dry powder; Non-flowing hydrated gel state. | Superabsorbent material obtained by heated mixing to dissolve, slowly cooled to gel, then frozen, then thawed and dried at 50° C. then pulverized. | 48.0 | 20.5 |
| 13 | 17 | Agar:κ-carrageenan : guar gum = 2:2:1 Dry powder; Non-flowing hydrated gel state. | Superabsorbent material obtained by heated mixing to dissolve, slowly cooled to gel, then frozen for direct freeze drying. | 57.0 | 21.8 |

TABLE 2-continued

Characterization of the Superabsorbent Materials

| Ex. No. | Samp. No. | Ingredients and ratio | Preparation Condition | Abs. ratio in water | Abs. ratio in gastric juice |
|---|---|---|---|---|---|
| 14 | 18 | Agar only Dry powder; Non-flowing hydrated gel state. | Superabsorbent material obtained by heated mixing to dissolve, slowly cooled to gel, then frozen, then thawed and dried at 50° C. then pulverized. | 68.0 | 18.5 |
| 15 | 19 | κ-carrageenan only Dry powder; Non-flowing hydrated gel state. | Superabsorbent material obtained by heated mixing to dissolve, slowly cooled to gel, then frozen for direct freeze drying. | 32.7 | 15.6 |
| 16 | 20 | Agar:konjac gum = 1:1 Dry powder; Non-flowing hydrated gel state. | Superabsorbent material obtained by heated mixing to dissolve, slowly cooled to gel, then frozen, then thawed and dried at 50° C. then pulverized. | 36.0 | 20.5 |
| 17 | 21 | κ-carrageenan:konjac gum = 1:1 Dry powder; Non-flowing hydrated gel state. | Superabsorbent material obtained by heated mixing to dissolve, slowly cooled to gel, then frozen for direct freeze drying. | 27.0 | 17.8 |

Example 18

Additional examples of the preparation and characterization of additional samples of the superabsorbent materials are shown in Table 3 below.

TABLE 3

Characterization of Additional Samples of Superabsorbent Materials

| | | | Thawing/drying at 50-60° C. | | Freeze-dry | |
|---|---|---|---|---|---|---|
| Sample No. | Ingredients and ratio | Concentration | water absorption ratio (pH 7) | water absorption ratio (pH 1) | water absorption ratio (pH 7) | water absorption ratio (pH 1) |
| 22 | agar | 1.20% | 11.9 | 9.2 | 30.2 | 22.4 |
| 23 | agar + konjac gum (1:1) | 0.6% + 0.6% | 18.4 | 19.3 | 43.7 | 41.0 |
| 24 | agar + konjac gum + carrageenan (10:1:1) | 1.0% + 0.1% + 0.1% | 13.1 | 12.0 | 33.2 | 27.9 |
| 25 | agar + konjac gum + carrageenan (2:1:1) | 0.6% + 0.3% + 0.3% | 31.3 | 21.5 | 56.9 | 37.8 |
| 26 | agar + konjac gum + carrageenan (1:1:1) | 0.4% + 0.4% + 0.4% | 58.8 | 36.1 | 66.9 | 48.8 |
| 27 | agar + konjac gum + carrageenan (2:5:5) | 0.2% + 0.5% + 0.5% | 67.6 | 46.4 | 89.2 | 58.8 |
| 28 | agar + konjac gum + xanthan gum (1:1:1) | 0.3% + 0.3% + 0.3% | 58.9 | 28.3 | n/a | n/a |
| 29 | agar + locust bean gum + carrageenan (1:1:1) | 0.4% + 0.4% + 0.4% | 34.2 | 24.0 | n/a | n/a |
| 30 | agar + locust bean gum + xanthan gum (1:1:1) | 0.3% + 0.3% + 0.3% | 44.9 | 20.3 | n/a | n/a |

TABLE 3-continued

Characterization of Additional Samples of Superabsorbent Materials

| Sample No. | Ingredients and ratio | Concentration | Thawing/drying at 50-60° C. | | Freeze-dry | |
|---|---|---|---|---|---|---|
| | | | water absorption ratio (pH 7) | water absorption ratio (pH 1) | water absorption ratio (pH 7) | water absorption ratio (pH 1) |
| 31 | agar + konjac gum + xanthan gum (3:1:1) | 0.6% + 0.2% + 0.2% | 37.7 | 18.7 | n/a | n/a |
| 32 | agar + locust bean gum + carrageenan (3:1:1) | 0.6% + 0.2% + 0.2% | 20.3 | 16.1 | n/a | n/a |

This batch of the samples were prepared by weighing each ingredient and add to deionized water at the ratio and mass concentration as indicated in Table 3, heating to 100° C. and stirring until all ingredients are fully dissolved. Each solution was cooled to 20° C. and stored in a 20° C. incubator for 6 hours, to form a stable gel. After 6 hours, the samples were transferred to a −20° C. freezer to store for 10 hours, thereby to obtain cryo-stabilized gel. After 10 hours, the cryo-stabilized gel was thawed at room temperature, excess water was filtered off, and the sample was further air dried in a 50° C. incubator. Alternatively, after 10 hours of cryogelation at −20° C., the sample was lyophilized to dry where the gel was pre-frozen until its center reached −40° C., and the sample was kept below −10° C. throughout the lyophilization process until the sample was dry. The dried sample was pulverized to 20 mesh to obtain the powdered superabsorbent materials. The absorption ratio at different pH conditions was measured as described above.

As shown in Table 3, freeze-dry generally led to a higher water absorption ratio than thawing dry. Since drying process was after the gel formation (20° C. for 6 hours) and stabilization by cryogelation (−20° C. for 10 hours), it is unlikely that the freezing methods will produce different structures. However, during thawing dry process, it is likely that the water was melted and some of the pores were collapsed. While most of the pore can be reformed upon rehydration, a fraction of pores may not be re-established, presumably because some of the surfaces that form the wall of the pore become associated with each other so strongly that they cannot be separated upon rehydration. By contrast, during freeze dry process, the water remained in its solid form and removed by sublimation, so the pore structure may be better maintained. The types of materials also contributed to different properties of the superabsorbent materials. As shown in Table 3, Sample Nos. 22-25 demonstrated significantly different properties in the samples prepared by two different drying methods, suggesting their pore structures are more sensitive to the drying methods, whereas Sample Nos. 26 and 27 are less sensitive.

Example 19

This example demonstrates the volume expansion and shape stability of Sample Nos. 22-32. Sample Nos. 22-32 were soaked in deionized water for 24 hours, and images of a particle of each sample were taken before and after rehydration using a Leica light microscope (model MZ125). Sample No. 22 showed low volume expansion but had a well-defined shape. Sample No. 23 showed low to modest volume expansion and had a well-defined shape. Sample No. 24 showed a sheet-like expansion, appeared to be an inter-connected bundle of fibers but did not have a well-defined gel matrix shape. Sample No. 25 showed low-to-modest volume expansion and the shape appeared to be stacked sheets. Sample No. 26 showed high volume expansion but appeared to have an inter-connected, heterogeneous sheet structures. Sample No. 27 showed large volume expansion. After fully swollen, Sample No. 27 had a well-defined shape that appeared to have a homogeneous gel matrix structure. Sample No. 28 showed high volume expansion but appeared to have an inter-connected, heterogeneous sheet structures. Sample No. 29 showed good volume expansion and good shape structure as a well-defined homogeneous gel matrix structure. Sample Nos. 30 and 31 were similar to Sample No. 29 and showed good volume expansion and good shape structure as a well-defined homogeneous gel matrix structure. Sample No. 32 was similar to Sample No. 24 and showed a sheet-like expansion, appeared to be an inter-connected bundle of fibers but did not have a well-defined gel matrix shape. Thus, various samples expanded in volume upon rehydration, and the degree of volume expansion generally correlated with the water absorption ratio measured by weight. However, not all samples had a well-defined shape upon rehydration. For examples, Sample Nos. 24, 28, and 33, and to a lesser degree also Sample No. 26, had a looser structure in the rehydrated form. By contrast, Sample No. 27 had the best maintained shape.

Example 20

This example demonstrates the water absorption ratio and volume expansion kinetics of Sample No. 27. Kinetic analysis of water absorption and volume expansion was performed on Sample No. 27. A dry particle of Sample No. 27 was swelled in deionized water (pH7) and the length of the particle was at various time points. The kinetic analysis showed that the sample particle underwent volume expansion rapidly upon rehydration, more than doubling its size in less than 6 minutes, expanding volume by 16-fold in 19 minutes, and eventually reaching a volume that was approximately 120-fold of the original volume of the dry particle. Most of the expansion was completed within 100 minutes (reaching 90% of the maximally expanded volume).

Example 21

This example demonstrates the scanning electron microscopic imaging (SEM) analysis of various samples. Sample Nos. 22-32 from thawing-dry preparation were Sputter coater coated with Pt and imaged on a JOEL JSM-7001 Scanning electron microscope. SEM images for Sample Nos, 22, 23, 24, and 27 were obtained from thawing dry. Although different samples showed various surface features, it was hard to determine if such features were intrinsic to a given composite nature polysaccharide material, because the particle surface may be affected by the pulverization processes. Sample No. 27, and to a lesser degree also Sample No. 24, showed some parallelly organized surface structure as compared to the other two samples. However, the correlation to the functionalities such as water absorption and volume expansion of this observation is unclear. In general, the samples prepared by thawing-dry did not show any porous structures. However, by water absorption ratio measurement and volume expansion, these samples showed substantial ability to absorb water and expand in volume upon rehydration, suggesting that the matrix structure of the composite polysaccharide material is largely preserved in the thawing-dry process and can be fully or substantially established upon rehydration.

Example 22

This example demonstrates the scanning electron microscopic imaging (SEM) analysis of hydrated samples prepared by flash freezing and freeze-drying at different pH conditions: at pH 7 and at pH 1, respectively. To capture the structural features in the hydrated state, thawing-dried samples from Table 3 were soaked in deionized water (pH=7 or pH=1) for at least 12 hours, flash frozen in liquid nitrogen, and lyophilized to dry, sputter coated with platinum and imaged on a JOEL JSM-7001 Scanning electron microscope. For each sample, a number of particles were imaged. At pH 7, Sample No. 22 had a relatively dense structure, and may include some layered structural feature at the surface, which could be responsible for a certain level of water absorption observed with this sample. Sample No. 23 showed a cross-layered pore structure on one face and a fibrous pore structure on the other face. Although some samples had a puffy appearance, the pore size seemed to be very small. Sample No. 24 showed a parallel-layered structure. The zoom-in view showed that each layer contains a network of small pores. Sample No. 25 showed a parallel-layered structure. The zoom-in view shows that each layer contained a network of pores that were approximately 1-5 µm wide, and 5-10 µm long, these pores were interconnected and intertwined with each other. Sample No. 26 showed a very porous structure but the pore structural pattern was less well-defined. Its surface did show a pattern of cross-layered pore. Sample No. 27 showed a characteristic parallel-layered large pore (10-20 µm wide, and 100-200 µm long) that seemed to be very deep. In another cross-section, the parallel-layered large pore seemed to be connected by many thin fibers. Sample No. 28 had a very porous structure that showed cross-layered pore pattern on one face and a puffy loose parallel fiber structure on the other. Sample No. 29 had a porous structure that resembled the pattern of fish scale on one face and layered sheets on the other. Sample No. 30 had a porous structure that seemed to be intertwined on one face and parallelly aligned on the other. Sample No. 31 had the structural features of parallel layers and honeycomb-like pore. Sample No. 32 had a loose layered structural feature on one face and a more densely packed layer structure on the other face.

The structural features of samples hydrated in pH 1 solution were generally similar to those observed with samples hydrated in pH 7 solution, although the pore size seemed to be smaller (for example, comparing pore size of Sample No. 25 at pH 7 and pH 1). These analyses strongly suggest that the structural features observed were stable under different conditions and that the highly reproducible structural features were likely intrinsic property of each composite natural polysaccharide.

Example 23

This example demonstrates the scanning electron microscopic imaging (SEM) analysis of hydrated samples prepared by freeze drying. The samples were prepared by freeze drying (see the last two columns of Table 3). Briefly, the samples were prepared by weighing each ingredient and adding to deionized water at the ratio and mass concentration as indicated in Table 3, heating to 100° C. and stirring until all ingredients are fully dissolved. Each solution was cooled to 20° C. and stored in a 20° C. incubator for 6 hours, to form a stable gel. After 6 hours, the samples were transferred to a −20° C. freezer to store for 10 hours, thereby to obtain a cryo-stabilized gel. After 10 hours, the cryo-stabilized gel was pre-frozen until its center reached −40° C. and subjected to lyophilization. The sample was kept below −10° C. throughout the lyophilization process until the sample was dry.

To capture the structural features in the hydrated state of freeze-dried samples from Table 3 (last two columns), sample particles were soaked in deionized water (pH=7) for more than 12 hours, flash frozen in liquid nitrogen, and lyophilized to dry, sputter coated with platinum and imaged on a JOEL JSM-7001 Scanning electron microscope. For each sample, a number of particles were imaged, images most representative of the observed structural features of a given sample are shown.

Sample No. 22 from freeze drying had a relatively dense structure with some layered structural feature at the surface, which could be responsible for a certain level of water absorption observed with this sample. Sample No. 23 from freeze drying showed a cross-layered pore structure; when viewed at the cross-section the interconnected pore structure was apparent. Sample No. 23 shows a fibrous pore structure from a different perspective. Sample 24 from freeze-drying showed a fine parallel-layered structure on the surface. The cut cross-section shows that each layer contained a network of pores. Sample 25 from freeze drying showed a parallel-layered structure on the surface. The zoom-in view showed that each layer contained a network of pores that were approximately 1-5 µm wide, and 5-10 µm long, these pores were interconnected and intertwined with each other. Sample No. 26 from freeze drying showed a very porous structure, but the pore structural pattern was less well-defined. Its surface did show a pattern of cross-layered pore. Sample No. 27 from freeze drying showed a characteristic interconnected pore pattern. The parallel-layered was also apparent on the surface. Overall, the structural features and pore pattern of freeze-dried samples in this example were similar to those observed for corresponding samples prepared by thawing-drying, although the pore sizes and the overall dry volume of the samples prepared by freeze drying were larger than their counterparts prepared by thawing drying, especially for Sample Nos. 22-25.

TREATMENT EXAMPLES

Example 24: Materials and Methods

Experiments were conducted to determine the effect of the superabsorbent material for a treatment to reduce cholesterol. The superabsorbent material was studied in a diet-induced obesity (DIO) mouse model to determine changes in food intake, bodyweight, lipids (e.g., including cholesterol), gastrointestinal function, and other parameters as described herein.

Mouse

A mouse model for obesity and diabetes was obtained and used in the studies. The mouse model was the C57Bl/6 mouse, where the mice were obtained from Jackson Lab at age 6-7 weeks and a weight of about 25-30 grams. Seven days of acclimation time was applied to the mice. The mice were housed in a ventilated cage rack system on a 12 hour light/dark cycle (lights on 7:00 AM). There were 4 mice per cage. Standard rodent chow and water were provided to the mice ad libitum, which included 60% kcal high-fat diet (HFD; Research Diet D12492, pellet).

Test Groups

The superabsorbent material was prepared into the mouse feed. The superabsorbent material was formulated with the high-fat diet and delivered to the test mice in the same manner as the HFD treatment was provided. For example, 25 mg of superabsorbent material (e.g., Product A: Example 7, Sample 11) was provided for consumption per day for each mouse for a period of 8 weeks. After seven days of acclimation, the mice were randomized into different groups based on bodyweights. The mice were divided into groups, each group having 10 mice based on the groups with the same diets: (Group 1) Standard Diet (e.g., standard rodent chew diet), (Group 2) High-fat Diet (HFD), and (Group 3) High-fat Diet and Treatment 1 (HFD+Product A). The mice were dosed with the test diets of the different groups. The dosing of test diets began on day 1 at the same time as the food induction and the study duration was 56 days.

Weekly Data Acquisition

The mice were treated with the test diets for a period of weeks. During the test period, the two-hour fasting blood glucose and body weights were measured once a week. The food intake was measured twice a week by: on Monday weighing food that was placed in the cage-top hopper; and on Friday weighing the leftover food.

Fecal Output Test

At the end of the study, mice were fed ad libitum until the acclimation period. Then mice were weighed, singly housed in polyurethane cages without access to food, and acclimate to the procedure room at least 30 minutes prior to the study. At each subsequent hour after administration up to 4 hours, the number of fecal pellet per animal and the weight of all fecal pellet produced per animal in each hour period were recorded. All collected fecal samples were snap frozen and stored at −80 C.

Blood Analysis

After the completion of the study, all mice were subjected to blood/serum collection via cardiac puncture. The serum was obtained and then analyzed for various health markers. The analysis included measuring lipid health markers with a lipid panel, which includes total cholesterol, high-density lipoproteins (HDL) and low-density lipoprotein (LDL). The HDL and LDL include cholesterol (HDL-C and LDL-C). Additionally, the analysis included measuring metabolic health markers for appetite regulating hormone analysis, which includes insulin and leptin.

Example 25: Body Weight

The mice were weighed weekly as indicated, the bodyweight of all mice were recorded for the entire study. FIG. 1. includes a graph of data that shows the bodyweight in grams per day for the mice in the study, where the mice are in groups based on the diets: (Group 1) Standard Diet (e.g., standard rodent chew diet), (Group 2) High-fat Diet (HFD), and (Group 3) High-fat Diet and Treatment 1 (HFD+Product A). The bodyweight change percentage is calculated as (bodyweight change)/(baseline bodyweight)×100. Compared to the standard diet-fed control mice of Group 1, the high fat diet (HFD) treated mice of Group 2 showed significantly higher bodyweight change percentage after about Day 12. The bodyweight in grams is shown per day is shown in FIG. 1. For the first 12 days, the weights were relatively similar; however, day 12 marked a divergence where Group 2 mice started significantly faster weight gains. Compared with the HFD treated mice of Group 2, the Product A (HFD-PA) treated mice of Group 3 displayed significantly lower bodyweight change percentage after Day 22. The data suggests that the superabsorbent material of Product A can prevent or reduce high fat diet induced bodyweight gain. Data are mean±SEM and analyzed by two-way ANOVA as applicable (compared to HFD-Vehicle, n=10-14/group).

Example 26: Lipid/Cholesterol Levels

The lipid/cholesterol levels were analyzed as described. The blood lipid profile was assessed at the end of the study under fasting condition. FIG. 2 shows the LDL-C levels for Group 1 (standard diet), Group 2 (HFD treatment), and Group 3 (HFD+Product A treatment). As shown, the HFD treatment significantly increases the LDL-C in the mice. However, the addition of Product A in the Group 3 mice shows a decrease in the LDL-C. This shows that the Product A can inhibit the increase of LDL-C attributed to the HFD treatment. As such, the amount of LDL-C can be reduced by providing the Product A, especially in HFD diets.

FIG. 3 shows the HDL-C levels for Group 1 (standard diet), Group 2 (HFD treatment), and Group 3 (HFD+Product A treatment). As shown, the HFD treatment significantly increases the HDL-C in the mice. However, the addition of Product A in the Group 3 mice shows a decrease in the HDL-C. This shows that the Product A can inhibit the increase of HDL-C attributed to the HFD treatment. As such, the amount of HDL-C can be reduced by providing the Product A, especially in HFD diets.

Figure 4:
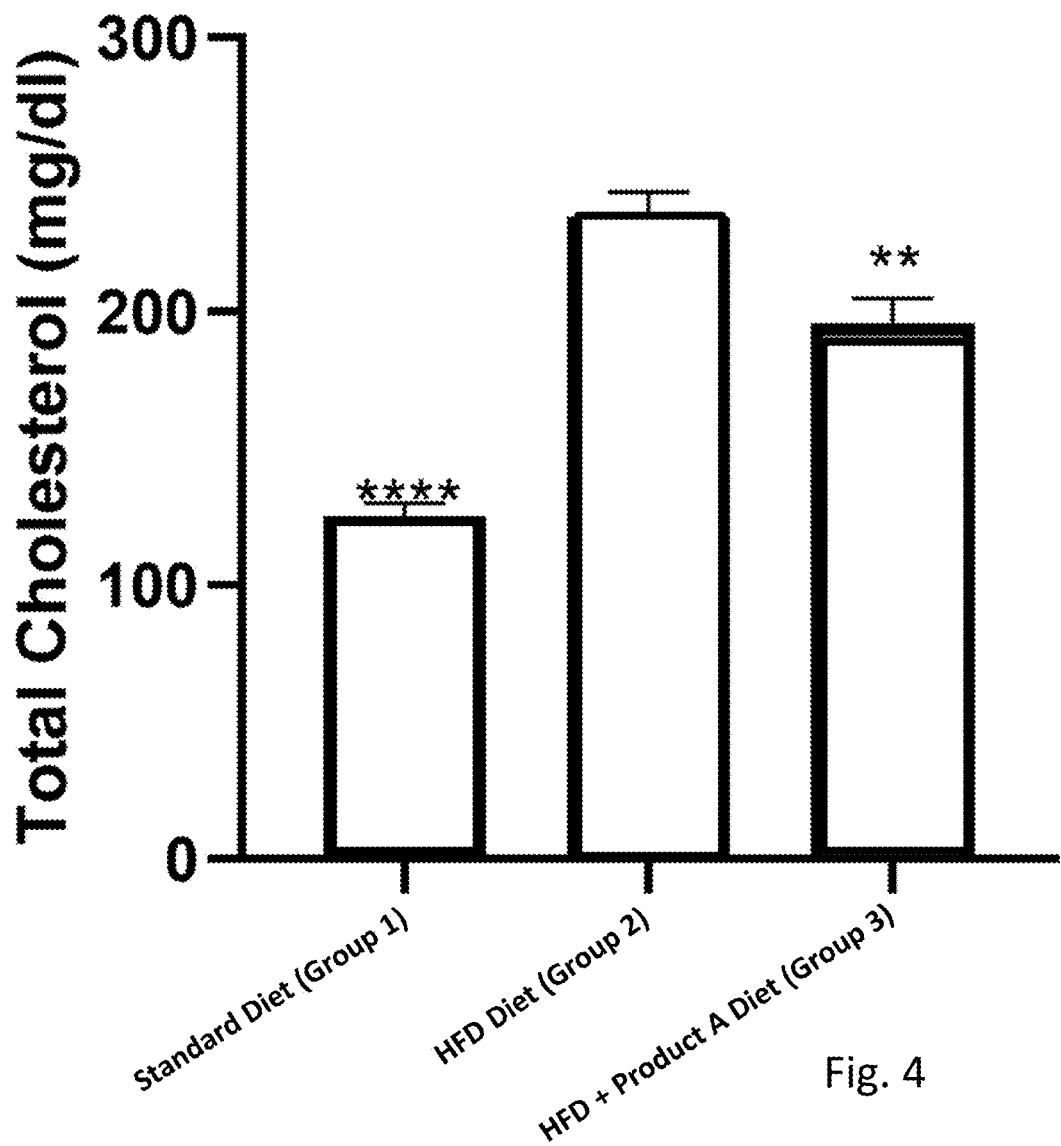
FIG. 4 includes a graph of data that shows the total cholesterol (TC) levels for Group 1 (standard diet), Group 2 (HFD treatment), and Group 3 (HFD+Product A treatment).

FIG. 4 shows the total cholesterol (TC) levels for Group 1 (standard diet), Group 2 (HFD treatment), and Group 3 (HFD+Product A treatment). As shown, the HFD treatment significantly increases the TC in the mice. However, the addition of Product A in the Group 3 mice shows a decrease in the TC. This shows that the Product A can inhibit the increase of TC attributed to the HFD treatment. As such, the amount of TC can be reduced by providing the Product A, especially in HFD diets.

The information from FIG. 2, FIG. 3 and FIG. 4 indicates that the Product A can reduce the total amount of lipid or cholesterol in the mice. Data are mean±SEM and analyzed by One-way ANOVA as applicable (compared to HFD-Vehicle, n=10-14/group). **:$p<0.0001$; :$p<0.01$; *$p<0.05$ vs. Group 2.

Compared to the standard diet-fed control mice (Group 1), the HFD treated mice (Group 2) had significantly higher levels of total cholesterol (TC), LDL-cholesterol (LDL-D), and HDL-cholesterol (HDL-C). The Group 3 mice that were treated with the HFD and Product A had lower total cholesterol (TC), LDL-cholesterol (LDL-D), and HDL-cholesterol (HDL-C) compared to the Group 2 mice, which indicates the improvement provided by the Product A.

Accordingly, product A can be provided to reduce (TC), LDL-cholesterol (LDL-D), and HDL-cholesterol (HDL-C).

Example 27: Hepatic Histopathological Evaluation

Fatty liver is well known to be associated with high cholesterol levels in a subject. As such, studying the liver for fatty liver can indicate the problems associated with high cholesterol. For light microscopic analysis of liver histology, the paraffin-embedded liver tissues were sliced into thin sections, and standard hematoxylin and eosin (H&E) staining was performed. A total of 9 fixed mouse liver samples (e.g., 3 treatment groups, 3 per group) were obtained from the mice. All liver tissue samples were processed and embedded with cross-section orientation. Each paraffin-embedded sample was sectioned at 4 μm onto positively charged slides.

Hematoxylin and Eosin (H&E)

H&E staining was performed on formalin-fixed paraffin-embedded (FFPE) mouse tissue sections following the Reveal Biosciences standard staining protocol. Hematoxylin, a basic dye, binds to acidic structures, such as nuclei, ribosomes, and rough endoplasmic reticulum (rER), which is visualized as a purplish blue color. Eosin, an acidic dye, stains basic structures, such as cytoplasm, pink. Individual sections were assessed for proper staining per standard quality control criteria.

Masson's Trichrome

Masson's trichrome staining was performed on formalin-fixed paraffin-embedded (FFPE) mouse tissue sections following Reveal Biosciences standard staining protocol. Three dyes are used to differentiate cells from surrounding connective tissue. Nuclei and basophilic structures are stained dark red or purple, cytoplasm, muscle, erythrocytes and keratin are stained red or pink, and connective tissue such as collagen is stained blue. Individual sections were assessed for proper staining per standard quality control criteria.

Image Data Acquisition

Whole slide images were generated using a Panoramic SCAN (3D Hitech). The imageDx™ workflow was used for image analysis, which is driven by advanced machine learning algorithms that perform automated image Quality Control (QC) assessments followed by the identification, classification, and quantitative measurement of disease features across the entire tissue. Data was generated by performing automated analysis of whole slide images. All tissue and staining artifacts were digitally excluded from the reported quantification. The analysis process began with automated identification of tissue on the slide, followed by segmentation of regions of interest, and then classification of positive and negative cells for quantification. These identified regions were then measured for precise positivity. Data is reported across the entire tissue.

Visual Liver Analysis

The liver was visually analyzed as shown in FIGS. 5, 6, and 7. FIG. 5 shows the normal liver under a standard chow diet (Group 1). FIG. 6 shows the liver when subjected to the HFD treatment (Group 2). FIG. 7 shows the liver when subjected to the HFD and Product A treatment (Group 3). As can be seen in a comparison between Group 1 and Group 2, the HFD significantly alters the liver tissue so that lighter colored regions are shown throughout. The lighter colored regions are indicative of oil droplets or fatty deposits in the liver, which are present in Group 2 with the HFD treatment, but substantially absent in Group 1 with the standard chow diet. The comparison shows that Group 2 has significantly elevated fatty liver, which appears as the lighter regions that visually look like lighter blooms surrounded by normal darker liver tissue. Additional white regions are also shown in Group 2 that are absent in Group 1, which also indicates the HFD diet causing changes in the liver morphology. The comparison of Group 2 and Group 3 shows that the addition of the Product A to the treatment as shown with Group 3 inhibits the formations shown in Group 2. That is, Group 3 omits the alterations in the liver tissue as minimal lighter colored regions are shown, and such regions are significantly smaller and not as clear as shown in Group 2. The Group 3 tissue does not include any lighter colored regions that are indicative of oil droplets or fatty deposits in the liver that are present in Group 2, and thereby the addition of Product A inhibits the negative effects of the HFD treatment. As such, the Product A can be used to inhibit the effects of a high fat diet.

Steatosis

The liver samples were analyzed for steatosis. Steatosis also called fatty change, is an abnormal retention of fat (lipids) within a cell or organ. Steatosis most often affects the liver (the primary organ of lipid metabolism) where the condition is commonly referred to as fatty liver disease (FLD), or non-alcoholic fatty liver disease (NAFLD) when not associated with alcohol. FIGS. 5, 6, and 7 show that the HFD can cause hepatocellular steatosis (no evidence of fibrosis), but the Product A can inhibit development of steatosis.

Additionally, the treatment with Product A was shown to have effects in liver lipid (e.g., percent lipid area and total lipid area), percent macro-vesicular, percent micro-vesicular, average vesicle size, and a steatosis score. The results are shown in Table 4. The data shows that Group 1 had lower percent lipid area, lower total area, lower percent micro-vesicular, and steatosis score compared to Group 2. This indicates that the HFD treatment causes increases in these values as shown. Notably, steatosis score is much higher in the Group 2 mice with the HFD treatment than normally treated mice in Group 1. However, the addition of Product A to the HFD in Group 3 shows lower percent lipid area, total lipid area percent micro-vesicular and steatosis score compared to Group 2. As a result, the Product A inhibits the effects of the HFD treatment by providing for lower lipid in the liver. Additionally, a comparison between Group 1 and Group 3 shows that the Group 3 treated mice had lower percent lipid and lower total lipid area than Group 1, which indicates that the Product A may have an overall lipid reduction, especially in liver. This also indicates that Product A may be useful for subjects with normal diets to inhibit lipid accumulation, such as in the liver or elsewhere.

TABLE 4

| Treatment | % Lipid Area | Total Lipid Area (mm^2) | % Macro-vesicular | % Micro-vesicular | Average Vesicle Size (um^2) | Tissue Area Analyzed (mm^2) | Steatosis Score |
| --- | --- | --- | --- | --- | --- | --- | --- |
| Group 1-1 | 0.29 | 0.05 | 73.40 | 26.60 | 47.82 | 17.82 | 0 |
| Group 1-2 | 0.22 | 0.04 | 79.80 | 20.20 | 73.95 | 19.59 | 0 |

TABLE 4-continued

| Treatment | % Lipid Area | Total Lipid Area (mm^2) | % Macro-vesicular | % Micro-vesicular | Average Vesicle Size (um^2) | Tissue Area Analyzed (mm^2) | Steatosis Score |
|---|---|---|---|---|---|---|---|
| Group 1-3_ | 0.18 | 0.03 | 78.25 | 21.75 | 57.74 | 18.39 | 0 |
| Group 2-13 | 9.71 | 2.52 | 48.77 | 51.23 | 26.53 | 26.00 | 3 |
| Group 2-14_ | 7.44 | 1.85 | 32.33 | 67.67 | 19.13 | 24.91 | 3 |
| Group 2-15 | 1.96 | 0.43 | 45.23 | 54.77 | 26.90 | 22.03 | 1 |
| Group 3-22 | 0.07 | 0.02 | 67.05 | 32.95 | 44.08 | 23.95 | 0 |
| Group 3-23 | 0.19 | 0.03 | 67.57 | 32.43 | 44.39 | 17.25 | 0 |
| Group 3-24 | 0.11 | 0.02 | 84.74 | 15.26 | 84.90 | 19.78 | 0 |

One skilled in the art will appreciate that, for the processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

As used herein, "prevent" or "prevented" or "preventing" or "prevention" refer to prevention or delay of the onset of a disorder, disease, or condition (e.g., increased cholesterol) and/or a decrease in the symptoms of high cholesterol in a subject relative to the symptoms of high cholesterol that would develop in the absence of the methods of the invention. The prevention can be complete, for example, the total absence of cholesterol increase to a high and unfavorable cholesterol level in a subject that undergoes the treatment described herein. The prevention of high cholesterol can also be partial, such that the cholesterol level in a subject has reduced symptoms from that which would have occurred without the present invention. The terms "prevention", "prophylactic treatment", and "prophylaxis" may be used interchangeable and are intended to refer to prevention.

The term "administered," "administering" or "administration" includes routes of administration which allow the superabsorbent material to perform their intended function(s) of preventing, mitigating, or treating high cholesterol in a subject, which can include oral consumption of the superabsorbent material. However, it may be possible that the superabsorbent material is formulated in a pharmaceutical composition for routes of administration other than oral consumption.

When used herein, the term "therapeutically effective amount" or "effective amount" includes an amount of the therapeutic or treatment composition that provides a prophylactic or therapeutic benefit in the treatment, prevention, or management of a disease or a symptom of a disease. The therapeutically effective amount may treat a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. The term "therapeutically effective amount" or "effective amount" of the superabsorbent material includes an amount of the superabsorbent material that is sufficient in treating, mitigating, or preventing high cholesterol. Alternatively an "effective amount" of the superabsorbent material means an amount of the superabsorbent material to be administered necessary to treat or prevent a disease or disorder mediated by high cholesterol.

A therapeutically effective amount can be readily determined on an individual basis and will be based, in part, on the severity of the high cholesterol level. Thus, a therapeutically effective amount of superabsorbent material can be determined by one of ordinary skill in the art using no more than routine experimentation in clinical management of a subject. For example, the specific amount that is therapeutically effective may be readily determined by an ordinary medical practitioner, and may vary depending on factors known in the art, such as, e.g. the type and location of infection, the patient's history (including genetic and medical history), sex, age, the patient's family history (including genetic and medical history), the patient's history of previous treatment modalities of obesity, the patient's history of progression of obesity, the stage of obesity, genetic risk of obesity, and the current administration of other therapeutic agents. Another factor influencing clinical management of a subject is the patient's side effect profile history. For example, a high fatty or otherwise high caloric diet may influence the determination of a specific treatment regimen of a subject in need of treatment, mitigation, or prevention of high cholesterol.

The dosage ranges for the administration of are those that produce the desired effect. Generally, the dosage will vary with the age, weight, condition, and sex of the patient, and the extent of disease. A person of ordinary skill in the art, given the teachings of the present specification, may readily determine suitable dosage ranges.

In some embodiments, a therapeutically effective amount of the superabsorbent material includes a precise dosage level determined by an attending physician or other health care provider and will depend upon well-known factors, including route of administration, and the age, body weight, sex, concomitant therapies, patient medical history including previous drug tolerances, general health of the patient; the nature, severity and clinical stage of obesity, and/or other clinical dosing factors known in the art.

The superabsorbent material can be a powder or prepared into any consumable having the powder. Also, the powder can be hydrated and gelled as described herein prior to consumption. However, an example administration is a pill or capsule of the superabsorbent material, or other suitable dosage form that may or may not include a pharmaceutically acceptable carrier.

Pharmaceutically acceptable carriers that may be useful in formulating pharmaceutical compositions of the present invention include but are not limited to lubricants, preservatives, stabilizers, solubilizers, penetrants, wetting agents, drying agents, bulking agents, fillers, emulsifiers, salts for influencing osmotic pressure, tonicity contributors (e.g., dextrose, mannitol, glycine and sodium chloride), buffers, antioxidants, colorings, flavorings and/or aromatic substances and the like which do not deleteriously react with the active compounds of the invention or each other.

Clearly, the skilled person can use other pharmaceutical formulations of the present invention containing superabsorbent materials. Pharmaceutical compositions of the present invention, and methods of forming such compositions, are described in detail by reference to standard textbooks such as Remington: The Science and Practice of Pharmacy, Twenty-Second Edition (Lippincott Williams & Wilkins, 2012); Handbook of Pharmaceutical Excipients, Seventh Edition (Pharmaceutical Press, 2012); Ansel's Pharmaceutical Dosage Forms and Drug Delivery Systems, Tenth Edition (Lippincott Williams & Wilkins, 2013); Modern Pharmaceutics, Fifth Edition (CRC Press, 2009); and in Harry's Cosmeticology, Ninth Edition (Chemical Publishing Company, 2015). Said standard textbooks are incorporated herein by reference in their entirety. Examples of suitable pharmaceutically acceptable carriers include water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, and the like. However, pure or otherwise formulated superabsorbent material can be prepared into capsules containing the powdered form.

Formulations of the superabsorbent material suitable for oral administration may be in the form of capsules, pills, wafers, tablets, lozenges, cachets, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and the like. In solid dosage forms for oral administration (capsules, tablets, wafers, pills, powders, granules and the like), the superabsorbent material can be mixed with one or more pharmaceutically acceptable carriers (e.g., sodium citrate, dicalcium phosphate, and/or any of the following: fillers or extenders, such as starches, lactose, sucrose, glucose, mannitol, and/or silicic acid; binders, (e.g., carboxymethylcellulose, gelatin, sucrose and acacia); humectants (e.g. glycerol); disintegrating agents (e.g. agar-agar, calcium carbonate, tapioca starch); solution-retarding agents (e.g. paraffin); absorption accelerators; wetting agents (e.g. cetyl alcohol); absorbents (e.g. kaolin); lubricants (e.g., talc, magnesium stearate, solid polyethylene glycols, sodium lauryl sulfate); and coloring agents). In the case of capsules, tablets and pills, the pharmaceutical compositions may also comprise suitable buffering agents. Solid compositions of a similar type may also be employed as fillers in soft and hard-filled gelatin or gelatin-type capsules (e.g., employing such excipients as lactose, high molecular weight polyethylene glycols, and the like).

A tablet may be made by compression or molding, optionally with one or more accessory ingredients. Compressed tablets may be prepared using binder, lubricant, inert diluent, preservative, disintegrant, and/or surface-active or dispersing agent. Molded tablets may be made, for example, by molding in a suitable machine a mixture of the powdered compound moistened with an inert liquid diluent. The tablets, and other solid dosage forms of the pharmaceutical compositions of the invention, such as capsules, pills, and granules/powders, may optionally be scored or prepared with coatings and shells, such as enteric coatings and other coatings well known in the pharmaceutical-formulating art.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:

1. A method for reducing cholesterol in a subject, comprising administering to the subject an effective amount of a superabsorbent material having a porous network structure without any chemical cross-linking; wherein the superabsorbent material is a dehydrated gel comprising agar, carrageenan, and konjac gum; and wherein the superabsorbent material has an absorption ratio of at least 10 in deionized water at 25° C.

2. The method of claim 1, wherein the method is to reduce the total cholesterol of the subject, to reduce the rate of a total cholesterol increase in the subject, or to increase the rate of a total cholesterol decrease in the subject.

3. The method of claim 1, wherein the method is to reduce cholesterol intake into the subject, to reduce cholesterol absorption by the gut of the subject, or to absorb cholesterol from the gut of the subject into the superabsorbent material.

4. The method of claim 1, wherein the method is to reduce low-density-lipoprotein cholesterol.

5. The method of claim 1, wherein the method is to reduce high-density-lipoprotein cholesterol.

6. The method of claim 1, comprising administering to the subject an effective amount of the superabsorbent material so that the subject has a slower rate of cholesterol gain, wherein the slower rate is compared to the rate of cholesterol gain of the subject prior to the administration of the superabsorbent material.

7. The method of claim 1, wherein the subject has a high fat diet prior to the administration of the superabsorbent material.

8. A method for reducing circulating lipid in a subject, comprising administering to the subject an effective amount of a superabsorbent material having a porous network structure without any chemical cross-linking; wherein the superabsorbent material is a dehydrated gel comprising agar, carrageenan, and konjac gum; and wherein the superabsorbent material has an absorption ratio of at least 10 in deionized water at 25° C.

9. The method of claim 8, wherein the method is to reduce the amount of a circulating lipid of the subject, to reduce the rate of a circulating lipid increase in the subject, or to increase the rate of a circulating lipid decrease in the subject.

10. The method of claim 8, wherein the method is to reduce low-density-lipoprotein.

11. The method of claim 8, wherein the method is to reduce high-density-lipoprotein.

12. The method of claim 8, comprising administering to the subject an effective amount of the superabsorbent material so that the subject has a slower rate of circulating lipid gain, wherein the slower rate is compared to the rate of circulating lipid gain of the subject prior to the administration of the superabsorbent material.

13. The method of claim 8, wherein the subject has a high fat diet prior to the administration of the superabsorbent material.

14. The method of claim 9, wherein the method is to reduce the amount of a circulating lipoprotein of the subject, to reduce the rate of a circulating lipoprotein increase in the subject, or to increase the rate of a circulating lipoprotein decrease in the subject.

15. The method of claim 14, wherein the lipoprotein is low-density-lipoprotein cholesterol.

16. The method of claim 14, wherein lipoprotein is high-density-lipoprotein cholesterol.

17. The method of claim 14, comprising administering to the subject an effective amount of the superabsorbent material so that the subject has a slower rate of circulating lipoprotein gain, wherein the slower rate is compared to the rate of circulating lipoprotein gain of the subject prior to the administration of the superabsorbent material, wherein the lipoprotein is low-density-lipoprotein cholesterol or high-density-lipoprotein cholesterol.

18. The method of claim 1, wherein the superabsorbent material comprises at least 10% by weight of agar.

19. The method of claim 1, wherein the superabsorbent material comprises at least 20% by weight of carrageenan.

20. The method of claim 1, wherein the superabsorbent material comprises agar, carrageenan, and konjac gum at a weight ratio of 10:1:1, 1:1:1, 1:1:2, 1:2:1, 2:1:1, or 2:5:5.

21. The method of claim 1, wherein the superabsorbent material comprises agar, carrageenan, and konjac gum at a weight ratio of 1:1:1, 1:1:2, or 1:2:1.

22. The method of claim 1, wherein the superabsorbent material has an absorption ratio of at least 20 or up to 200 in deionized water at 25° C.

23. The method of claim 1, wherein the superabsorbent material has an absorption ratio of at least 50 or up to 200 in deionized water at 25° C.

24. The method of claim 1, wherein the superabsorbent material has an absorption ratio of at least 100 or up to 200 in deionized water at 25° C.

25. The method of claim 8, wherein the superabsorbent material comprises at least 10% by weight of agar.

26. The method of claim 8, wherein the superabsorbent material comprises at least 20% by weight of carrageenan.

27. The method of claim 8, wherein the superabsorbent material comprises agar, carrageenan, and konjac gum at a weight ratio of 10:1:1, 1:1:1, 1:1:2, 1:2:1, 2:1:1, or 2:5:5.

28. The method of claim 8, wherein the superabsorbent material comprises agar, carrageenan, and konjac gum at a weight ratio of 1:1:1, 1:1:2, or 1:2:1.

29. The method of claim 8, wherein the superabsorbent material has an absorption ratio of at least 20 or up to 200 in deionized water at 25° C.

30. The method of claim 8, wherein the superabsorbent material has an absorption ratio of at least 50 or up to 200 in deionized water at 25° C.

31. The method of claim 8, wherein the superabsorbent material has an absorption ratio of at least 100 or up to 200 in deionized water at 25° C.

\* \* \* \* \*